United States Patent
Sakamoto et al.

(10) Patent No.: US 10,954,443 B2
(45) Date of Patent: Mar. 23, 2021

(54) POLYMERIZABLE COMPOUND, POLYMERIZABLE COMPOSITION, POLYMER, AND OPTICALLY ANISOTROPIC PRODUCT

(71) Applicant: ZEON CORPORATION, Tokyo (JP)

(72) Inventors: Kei Sakamoto, Tokyo (JP); Kumi Okuyama, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 119 days.

(21) Appl. No.: 16/512,704

(22) Filed: Jul. 16, 2019

(65) Prior Publication Data
US 2019/0359890 A1 Nov. 28, 2019

Related U.S. Application Data

(62) Division of application No. 15/115,987, filed as application No. PCT/JP2015/053517 on Feb. 9, 2015, now Pat. No. 10,400,170.

(30) Foreign Application Priority Data

Feb. 14, 2014 (JP) .................. 2014-026783

(51) Int. Cl.
| C09K 19/38 | (2006.01) |
| C07C 251/68 | (2006.01) |
| C08F 20/36 | (2006.01) |
| C08F 222/10 | (2006.01) |
| G02B 5/30 | (2006.01) |
| C07C 229/36 | (2006.01) |
| C08G 73/02 | (2006.01) |
| G02B 1/04 | (2006.01) |
| G02B 5/00 | (2006.01) |

(52) U.S. Cl.
CPC ........ $C09K\ 19/3838$ (2013.01); $C07C\ 229/36$ (2013.01); $C07C\ 251/68$ (2013.01); $C08F\ 20/36$ (2013.01); $C08F\ 222/10$ (2013.01); $C08F\ 222/1006$ (2013.01); $C08G\ 73/024$ (2013.01); $G02B\ 1/04$ (2013.01); $G02B\ 5/00$ (2013.01); $G02B\ 5/3083$ (2013.01)

(58) Field of Classification Search
CPC .. C09K 19/38; C09K 19/3838; C07C 229/36; C07C 251/68; C08F 20/36; C08F 222/10; C08F 222/1006; C08G 73/024; G02B 1/04; G02B 5/00; G02B 5/3083
USPC ........................................................ 526/312
See application file for complete search history.

(56) References Cited

U.S. PATENT DOCUMENTS

| 5,567,349 A | 10/1996 | Kelly et al. |
| 6,139,771 A | 10/2000 | Walba et al. |
| 6,203,724 B1 | 3/2001 | Reiffenrath et al. |

(Continued)

FOREIGN PATENT DOCUMENTS

| CN | 103459438 A | 12/2013 |
| CN | 103492363 A | 1/2014 |

(Continued)

OTHER PUBLICATIONS

Aug. 16, 2016, International Preliminary Report on Patentability issued in the International Patent Application No. PCT/JP2015/053517.

(Continued)

Primary Examiner — Geraldina Visconti
(74) Attorney, Agent, or Firm — Kenja IP Law PC

(57) ABSTRACT

Provided is a compound represented by the following formula:

(3)

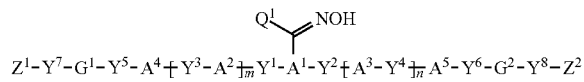

$Z^1-Y^7-G^1-Y^5-A^4 \{Y^3-A^2\}_m Y^1-A^1-Y^2 \{A^3-Y^4\}_n A^5-Y^6-G^2-Y^8-Z^2$ $Y^1$ to $Y^8$ each represent a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$—, or —NR$^1$—O—, R$^1$ being a hydrogen atom or an alkyl group having 1 to 6 carbon atoms. $G^1$ and $G^2$ each represent a divalent linear aliphatic group having 1 to 20 carbon atoms. that optionally includes —O—, —S—, —O—C(=O)—, —C(=O)—O—, —O—C(=O)—O—, —NR$^3$—C(=O)—, —C(=O)—NR$^3$—, —NR$^3$—, or —C(=O)—. $Z^1$ and $Z^2$ each represent an alkenyl group having 2 to 10 carbon atoms. $A^1$ represents a trivalent aromatic group. $A^2$ and $A^3$ each represent a divalent alicyclic hydrocarbon group having 3 to 30 carbon atoms. $A^4$ and $A^5$ each represents a divalent aromatic group having 6 to 30 carbon atoms. $Q^1$ represents a alkyl group having 1 to 6 carbon atoms, an organic group having 2 to 30 carbon atoms that includes at least one of an aromatic hydrocarbon ring and a heteroaromatic ring, or a hydrogen atom. n and m each represent 0 or 1.

2 Claims, No Drawings

(56) References Cited

U.S. PATENT DOCUMENTS

| | | | |
|---|---|---|---|
| 6,565,974 B1 | 5/2003 | Uchiyama et al. | |
| 9,029,490 B2 | 5/2015 | Sakamoto et al. | |
| 9,150,677 B2 | 10/2015 | Sakamoto et al. | |
| 9,207,360 B2 | 12/2015 | Sakamoto et al. | |
| 10,400,170 B2 * | 9/2019 | Sakamoto | C08G 73/024 |
| 2002/0159005 A1 | 10/2002 | Arakawa et al. | |
| 2003/0102458 A1 | 6/2003 | Nishikawa et al. | |
| 2007/0176145 A1 | 8/2007 | Nishikawa et al. | |
| 2007/0298191 A1 | 12/2007 | Yamahara et al. | |
| 2009/0072194 A1 | 3/2009 | Yamahara et al. | |
| 2009/0189120 A1 | 7/2009 | Takeuchi | |
| 2010/0201920 A1 | 8/2010 | Adlem et al. | |
| 2010/0301271 A1 | 12/2010 | Adlem et al. | |
| 2014/0107247 A1 | 4/2014 | Sakamoto et al. | |
| 2014/0142266 A1 | 5/2014 | Sakamoto et al. | |
| 2017/0166815 A1 * | 6/2017 | Sakamoto | C08F 222/10 |
| 2019/0359890 A1 * | 11/2019 | Sakamoto | C08F 20/36 |

FOREIGN PATENT DOCUMENTS

| | | |
|---|---|---|
| EP | 2698388 A1 | 2/2014 |
| EP | 2703385 A1 | 3/2014 |
| EP | 2871192 A1 | 5/2015 |
| GB | 2188048 A | 9/1987 |
| JP | H1068816 A | 3/1998 |
| JP | H1090521 A | 4/1998 |
| JP | H1152131 A | 2/1999 |
| JP | 2000284126 A | 10/2000 |
| JP | 2001004837 A | 1/2001 |
| JP | 2002267838 A | 9/2002 |
| JP | 2003160540 A | 6/2003 |
| JP | 2005208414 A | 8/2005 |
| JP | 2005208415 A | 8/2005 |
| JP | 2005208416 A | 8/2005 |
| JP | 2005289980 A | 10/2005 |
| JP | 2006330710 A | 12/2006 |
| JP | 2007002208 A | 1/2007 |
| JP | 2009173893 A | 8/2009 |
| JP | 2009179563 A | 8/2009 |
| JP | 2009274984 A | 11/2009 |
| JP | 2010030979 A | 2/2010 |
| JP | 2010031223 A | 2/2010 |
| JP | 2010537954 A | 12/2010 |
| JP | 2010537955 A | 12/2010 |
| JP | 2011006360 A | 1/2011 |
| JP | 2011006361 A | 1/2011 |
| JP | 2011042606 A | 3/2011 |
| WO | 0026705 A1 | 5/2000 |
| WO | 2006052001 A1 | 5/2006 |
| WO | 2012141245 A1 | 10/2012 |
| WO | 2012147904 A1 | 11/2012 |
| WO | 2012169424 A1 | 12/2012 |
| WO | 2012176679 A1 | 12/2012 |
| WO | 2013018526 A1 | 2/2013 |
| WO | 2014010325 A1 | 1/2014 |

OTHER PUBLICATIONS

Feb. 13, 2019, Communication pursuant to Article 94(3) EPC issued by the European Patent Office in the corresponding European Patent Application No. 15749351.1.

Sep. 6, 2017, Extended European Search Report issued by the European Patent Office in the corresponding European Patent Application No. 15749351.1.

\* cited by examiner ained on Japanese Patent
POLYMERIZABLE COMPOUND, POLYMERIZABLE COMPOSITION, POLYMER, AND OPTICALLY ANISOTROPIC PRODUCT

CROSS-REFERENCE TO RELATED APPLICATION

This application is a divisional application of U.S. application Ser. No. 15/115,987 filed Aug. 2, 2016, which is a National Stage Application of PCT/JP2015/053517 filed Feb. 9, 2015, which claims priority based on Japanese Patent Application No. 2014-026783 filed Feb. 14, 2014. The disclosures of the prior applications are hereby incorporated by reference herein in their entirety.

TECHNICAL FIELD

The present invention relates to a polymerizable compound, a polymerizable composition, and a polymer that can produce an optical film that achieves uniform conversion of polarized light over a wide wavelength band, and also relates to an optically anisotropic product.

BACKGROUND ART

A flat panel display (FPD) that utilizes an optical film (e.g., polarizer and retardation film) can achieve high-resolution display, and has been widely used as a display device that exhibits excellent performance.

A quarter-wave plate that converts linearly polarized light into circularly polarized light, a half-wave plate that changes the plane of vibration of linearly polarized light by 90°, and the like are known. Such a retardation film can achieve accurate conversion of specific monochromatic light so that ¼λ or ½λ retardation occurs.

However, a known retardation film has a problem in that polarized light that passes through is converted into colored polarized light. Specifically, since a material that forms the retardation film has wavelength dispersion with respect to retardation, and a polarization state distribution corresponding to each wavelength occurs with respect to white light that includes different light rays in the visible region, it is impossible to achieve accurate ¼λ or ½λ retardation over the entire wavelength band.

In order to solve the above problem, various types of wideband retardation films that can achieve uniform retardation with respect to light over a wide wavelength band (i.e., retardation films having reverse wavelength dispersion) have been studied (see Patent Literature 1 to 6, for example).

It has been desired to reduce the thickness of a flat panel display as much as possible along with an improvement in performance and widespread use of mobile information terminals (e.g., mobile personal computers and mobile phones). Therefore, a reduction in thickness of the retardation film has also been desired.

It has been considered that it is most effective to produce a retardation film by applying a polymerizable composition that includes a low-molecular-weight polymerizable compound to a film substrate in order to reduce the thickness of the retardation film. Various low-molecular-weight polymerizable compounds having excellent wavelength dispersion, and various polymerizable compositions using such polymerizable compounds have been developed (see Patent Literature 7 to 24, for example).

However, the low-molecular-weight polymerizable compounds or the polymerizable compositions disclosed in Patent Literature 7 to 24 have a number of problems in that reverse wavelength dispersion may be insufficient, or it may be difficult to apply the low-molecular-weight polymerizable compounds or the polymerizable compositions to a film due to a high melting point that is not suitable for an industrial process, or the temperature range in which liquid crystallinity is obtained may be very narrow, or solubility in a solvent generally used for an industrial process may be low. Moreover, since these low-molecular-weight polymerizable compounds and the like are synthesized by performing a plurality of steps using a synthesis method that utilizes an expensive reagent, the production cost increases.

CITATION LIST

Patent Literature

Patent Literature 1: JP-A-10-68816
Patent Literature 2: JP-A-10-90521
Patent Literature 3: JP-A-11-52131
Patent Literature 4: JP-A-2000-284126 (US20020159005A1)
Patent Literature 5: JP-A-2001-4837
Patent Literature 6: WO2000/026705
Patent Literature 7: JP-A-2002-267838
Patent Literature 8: JP-A-2003-160540 (US20030102458A1)
Patent Literature 9: JP-A-2005-208414
Patent Literature 10: JP-A-2005-208415
Patent Literature 11: JP-A-2005-208416
Patent Literature 12: JP-A-2005-289980 (US20070176145A1)
Patent Literature 13: JP-A-2006-330710 (US20090072194A1)
Patent Literature 14: JP-A-2009-179563 (US20090189120A1)
Patent Literature 15: JP-A-2010-31223
Patent Literature 16: JP-A-2011-6360
Patent Literature 17: JP-A-2011-6361
Patent Literature 18: JP-A-2011-42606
Patent Literature 19: JP-T-2010-537954 (US20100201920A1)
Patent Literature 20: JP-T-2010-537955 (US20100301271A1)
Patent Literature 21: WO2006/052001 (US20070298191A1)
Patent Literature 22: U.S. Pat. No. 6,139,771
Patent Literature 23: U.S. Pat. No. 6,203,724
Patent Literature 24: U.S. Pat. No. 5,567,349

SUMMARY OF INVENTION

Technical Problem

The invention was conceived in view of the above situation. An object of the invention is to provide a polymerizable compound, a polymerizable composition, and a polymer that have a practical low melting point, exhibit excellent solubility in a general-purpose solvent, can be produced at low cost, and can produce an optical film that achieves uniform conversion of polarized light over a wide wavelength band, as well as an optically anisotropic product.

Solution To Problem

The inventors conducted extensive studies in order to solve the above problem. As a result, the inventors found that a polymerizable compound represented by the following formula (I), a polymerizable composition that includes the polymerizable compound and an initiator, and a polymer obtained by polymerizing the polymerizable compound or the polymerizable composition have a practical low melting point, exhibit excellent solubility in a general-purpose solvent, can be produced at low cost, and can produce an optically anisotropic product that achieves uniform conversion of polarized light over a wide wavelength. This finding has led to the completion of the invention.

Several aspects of the invention provide the following polymerizable compound (see (1) to (7)), polymerizable composition (see (8) and (9)), polymer (see (10) and (11)), and optically anisotropic product (see (12)).

(1) A polymerizable compound represented by the following formula (I),

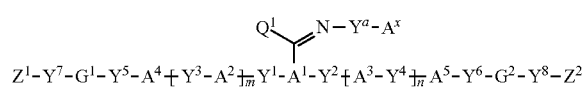

(I)

wherein each of $Y^1$ to $Y^8$ independently represents a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$—, or —NR$^1$—O—, R$^1$ represents a hydrogen atom or an alkyl group having 1 to 6 carbon atoms, $Y^a$ represents —O—, —S—, —O—C(=O)—, —C(=O)—O—, —O—C(=O)—O—, —C(=O)—NR$^2$—, —O—C(=O)—NR$^2$—, or —O—NR$^2$—, R$^2$ represents a hydrogen atom or an alkyl group having 1 to 6 carbon atoms, each of $G^1$ and $G^2$ independently represents a substituted or unsubstituted divalent linear aliphatic group having 1 to 20 carbon atoms that optionally includes —O—, —S—, —O—C(=O)—, —C(=O)—O—, —O—C(=O)—O—, —NR$^3$—C(=O)—, —C(=O)—NR$^3$—, —NR$^3$—, or —C(=O)—, provided that a case where the linear aliphatic group includes two or more contiguous —O— or —S— is excluded, R$^3$ represents a hydrogen atom or an alkyl group having 1 to 6 carbon atoms, each of $Z^1$ and $Z^2$ independently represents an alkenyl group having 2 to 10 carbon atoms that is substituted with a halogen atom, or unsubstituted, $A^x$ represents an organic group having 2 to 30 carbon atoms that includes at least one aromatic ring selected from the group consisting of an aromatic hydrocarbon ring and a heteroaromatic ring, $A^1$ represents a substituted or unsubstituted trivalent aromatic group, each of $A^2$ and $A^3$ independently represents a substituted or unsubstituted divalent alicyclic hydrocarbon group having 3 to 30 carbon atoms, each of $A^4$ and $A^5$ independently represents a substituted or unsubstituted divalent aromatic group having 6 to 30 carbon atoms, $Q^1$ represents a substituted or unsubstituted alkyl group having 1 to 6 carbon atoms, an organic group having 2 to 30 carbon atoms that includes at least one aromatic ring selected from the group consisting of an aromatic hydrocarbon ring and a heteroaromatic ring, or a hydrogen atom, and each of m and n independently represents 0 or 1.

(2) The polymerizable compound according to (1), wherein the total number of π electrons included in $A^x$ is 4 to 24.

(3) The polymerizable compound according to (1) or (2), wherein $A^1$ is a substituted or unsubstituted trivalent benzene ring group, or a substituted or unsubstituted trivalent naphthalene ring group.

(4) The polymerizable compound according to any one of (1) to (3), wherein each of $Y^1$ to $Y^8$ is independently a chemical single bond, —O—, —O—C(=O)—, —C(=O)—O—, or —O—C(=O)—O—.

(5) The polymerizable compound according to any one of (1) to (4), wherein each of $Z^1$ and $Z^2$ is independently $CH_2$=CH—, $CH_2$=C($CH_3$)—, or $CH_2$=C(Cl)—.

(6) The polymerizable compound according to any one of (1) to (5), wherein each of $G^1$ and $G^2$ is independently a substituted or unsubstituted divalent aliphatic group having 1 to 12 carbon atoms that optionally includes —O—, —O—C(=O)—, —C(=O)—O—, or —C(=O)—, provided that a case where the aliphatic group includes two or more contiguous —O— is excluded.

(7) The polymerizable compound according to any one of (1) to (6), wherein each of $G^1$ and $G^2$ is independently an alkylene group having 1 to 12 carbon atoms.

(8) A polymerizable composition including at least one polymerizable compound according to any one of (1) to (7).

(9) A polymerizable composition including at least one polymerizable compound according to any one of (1) to (7), and an initiator.

(10) A polymer obtained by polymerizing the polymerizable compound according to any one of (1) to (7), or polymerizing the polymerizable composition according to (8) or (9).

(11) The polymer according to (10), the polymer being a liquid crystal polymer.

(12) An optically anisotropic product including the polymer according to (11).

Advantageous Effects of Invention

The polymerizable compound, the polymerizable composition, and the polymer according to the aspects of the invention make it possible to inexpensively produce an optically anisotropic product that achieves uniform conversion of polarized light over a wide wavelength band, and exhibits satisfactory performance.

Since the optically anisotropic product according to one aspect of the invention is produced using the polymerizable compound, the polymerizable composition, or the polymer according to one aspect of the invention, the optically anisotropic product can be produced at low cost, can achieve uniform conversion of polarized light over a wide wavelength band, and exhibits satisfactory performance.

An antireflective film may be produced by combining the optically anisotropic product according to one aspect of the invention that is formed in the shape of a film with a polarizer. The antireflective film may suitably be used as an antireflective film for a touch panel or an organic electroluminescence device, for example.

DESCRIPTION OF EMBODIMENTS

A polymerizable compound, a polymerizable composition, a polymer, and an optically anisotropic product according to the exemplary embodiments of the invention are described in detail below.

1) Polymerizable Compound

A polymerizable compound according to one embodiment of the invention is a compound represented by the formula (I) (hereinafter may be referred to as "polymerizable compound (I)").

Each of $Y^1$ to $Y^8$ in the formula (I) independently represents a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —N$^1$—C(=O)—NR$^1$—, —O—NR$^1$—, or —NR$^1$—O—.

$R^1$ represents a hydrogen atom or an alkyl group having 1 to 6 carbon atoms.

Examples of the alkyl group having 1 to 6 carbon atoms represented by $R^1$ include a methyl group, an ethyl group, an n-propyl group, an isopropyl group, an n-butyl group, a sec-butyl group, a t-butyl group, an n-pentyl group, an n-hexyl group, and the like.

$R^1$ preferably represents a hydrogen atom or an alkyl group having 1 to 4 carbon atoms.

It is preferable that each of $Y^1$ to $Y^8$ included in the polymerizable compound according to one embodiment of the invention be independently a chemical single bond, —O—, —O—C(=O)—, —C(=O)—O—, or —O—C(=O)—O—.

$Y^a$ represents —O—, —S—, —O—C(=O)—, —C(=O)—O—, —O—C(=O)—O—, —C(=O)—NR$^2$—, —O—C(=O)—NR$^2$—, or —O—NR$^2$—. $R^2$ represents a hydrogen atom or an alkyl group having 1 to 6 carbon atoms (mentioned above in connection with $R^1$).

It is preferable that $Y^a$ be —O—C(=O)— or —O—, and more preferably —O—C(=O)—.

Each of $G^1$ and $G^2$ independently represents a substituted or unsubstituted divalent linear aliphatic group having 1 to 20 carbon atoms. Note that the expression "substituted or unsubstituted" used herein in connection with a group or the like means that the group or the like is unsubstituted, or substituted with a substituent (hereinafter the same).

Examples of the divalent linear aliphatic group having 1 to 20 carbon atoms include an alkylene group having 1 to 20 carbon atoms, such as a methylene group, an ethylene group, a trimethylene group, a propylene group, a tetramethylene group, a pentamethylene group, a hexamethylene group, an octamethylene group, and a decamethylene group(—(CH$_2$)$_{10}$—); an alkenylene group having 2 to 20 carbon atoms, such as a vinylene group, a 1-methylvinylene group, a propenylene group, a 1-butenylene group, a 2-butenylene group, a 1-pentenylene group, and a 2-pentenylene group; and the like.

Examples of a substituent that may substitute the divalent linear aliphatic group represented by $G^1$ and $G^2$ include a halogen atom such as a fluorine atom, a chlorine atom, a bromine atom, and an iodine atom; an alkoxy group having 1 to 6 carbon atoms, such as a methoxy group, an ethoxy group, an n-propoxy group, an isopropoxy group, an n-butoxy group, a sec-butoxy group, a t-butoxy group, an n-pentyloxy group, and an n-hexyloxy group; and the like. Among these, a fluorine atom, a methoxy group, and an ethoxy group are preferable.

The linear aliphatic group optionally includes —O—, —S—, —O—C(=O)—, —C(=O)—O—, —O—C(=O)—O—, —NR$^3$—C(=O)—, —C(=O)—NR$^3$—, —NR$^3$—, or —C(=O)—, provided that a case where the linear aliphatic group includes two or more contiguous —O— or —S— is excluded. $R^3$ represents a hydrogen atom or an alkyl group having 1 to 6 carbon atoms (mentioned above in connection with $R^1$), and is preferably a hydrogen atom or a methyl group.

—O—, —O—C(=O)—, —C(=O)—O—, and —C(=O)— are preferable as the group that is optionally included in the linear aliphatic group.

Specific examples of the linear aliphatic group that includes the above group include —CH$_2$—CH$_2$—O—CH$_2$—CH$_2$—, —CH$_2$—CH$_2$—S—CH$_2$—CH$_2$—, —CH$_2$—CH$_2$—O—C(=O)—CH$_2$—CH$_2$—, —CH$_2$—CH$_2$—C(=O)—O—CH$_2$—CH$_2$—, —CH$_2$—CH$_2$—C(=O)—O—CH$_2$—, —CH$_2$—O—C(=O)—O—CH$_2$—CH$_2$—, —CH$_2$—CH$_2$—NR$^3$—C(=O)—CH$_2$—CH$_2$—, —CH$_2$—CH$_2$—C(=O)—NR$^3$—CH$_2$—, —CH$_2$—NR$^3$—CH$_2$—CH$_2$—, —CH$_2$—C(=O)—CH$_2$—, and the like.

It is preferable that each of $G^1$ and $G^2$ be independently a substituted or unsubstituted divalent linear aliphatic group having 1 to 12 carbon atoms that optionally includes —O—, —O—C(=O)—, —C(=O)—O—, or —C(=O)—, provided that a case where the aliphatic group includes two or more contiguous —O— is excluded, more preferably a divalent linear aliphatic group such as an alkylene group having 1 to 12 carbon atoms or an alkenylene group having 2 to 20 carbon atoms, still more preferably an alkylene group having 1 to 12 carbon atoms, and particularly preferably a tetramethylene group (—(CH$_2$)$_4$—), a hexamethylene group (—(CH$_2$)$_6$—), an octamethylene group (—(CH$_2$)$_8$—), or a decamethylene group (—(CH$_2$)$_{10}$—).

Each of $Z^1$ and $Z^2$ independently represents an alkenyl group having 2 to 10 carbon atoms that is substituted with a halogen atom, or unsubstituted.

The number of carbon atoms of the alkenyl group is preferably 2 to 6. Examples of the halogen atom that may substitute the alkenyl group include a fluorine atom, a chlorine atom, a bromine atom, and the like. Among these, a chlorine atom is preferable.

Specific examples of the alkenyl group having 2 to 10 carbon atoms represented by $Z^1$ and $Z^2$ include CH$_2$=CH—, CH$_2$=C(CH$_3$)—, CH$_2$=CH—CH$_2$—, CH$_3$—CH=CH—, CH$_2$=CH—CH$_2$CH$_2$—, CH$_2$=C(CH$_3$)—CH$_2$CH$_2$—, (CH$_3$)$_2$C=CH—CH$_2$—, (CH$_3$)$_2$C=CH—CH$_2$CH$_2$—, CH$_2$=C(Cl)—, CH$_2$=C(CH$_3$)—CH$_2$—, CH$_3$—CH=CH—CH$_2$—, and the like.

It is preferable that each of $Z^1$ and $Z^2$ be independently CH$_2$=CH—, CH$_2$=C(CH$_3$)—, CH$_2$=C(Cl)—, CH$_2$=CH—CH$_2$—, CH$_2$=C(CH$_3$)—CH$_2$—, or CH$_2$=C(CH$_3$)—CH$_2$CH$_2$—, more preferably CH$_2$=CH—, CH$_2$=C(CH$_3$)—, or CH$_2$=C(Cl)—, and particularly preferably CH$_2$=CH—, in order to ensure that the intended effects of the invention can be more advantageously achieved.

$A^x$ represents an organic group having 2 to 30 carbon atoms that includes at least one aromatic ring selected from the group consisting of an aromatic hydrocarbon ring and a heteroaromatic ring.

The term "aromatic ring" used herein refers to a cyclic structure that exhibits aromaticity in a broad sense according to Huckel's rule (i.e., a cyclic conjugated structure that includes (4n+2) π electrons, and a structure that exhibits aromaticity in which lone pairs of hetero atoms (e.g., sulfur, oxygen, or nitrogen) are involved in the π electron system (e.g., thiophene, furan, and benzothiazole)).

The total number of π electrons included in $A^x$ is preferably 4 to 24.

The organic group having 2 to 30 carbon atoms represented by $A^x$ that includes at least one aromatic ring selected from the group consisting of an aromatic hydrocarbon ring and a heteroaromatic ring, may include a plurality of aromatic rings, and may include an aromatic hydrocarbon ring and a heteroaromatic ring.

Examples of the aromatic hydrocarbon ring include a benzene ring, a naphthalene ring, an anthracene ring, and the like. Examples of the heteroaromatic ring include a monocyclic heteroaromatic ring such as a pyrrole ring, a furan ring, a thiophene ring, a pyridine ring, a pyridazine ring, a pyrimidine ring, a pyrazine ring, a pyrazole ring, an imidazole ring, an oxazole ring, and a thiazole ring; a fused heteroaromatic ring such as a benzothiazole ring, a benzoxazole ring, a quinoline ring, a phthalazine ring, a benzimidazole ring, a benzopyrazole ring, a benzofuran ring, a benzothiophene ring, a thiazolopyridine ring, an oxazolopyridine ring, a thiazolopyrazine ring, an oxazolopyrazine ring, a thiazolopyridazine ring, an oxazolopyridazine ring, a thiazolopyrimidine ring, and an oxazolopyrimidine ring; and the like.

The aromatic ring included in $A^x$ may be substituted with a substituent. Examples of the substituent include a halogen atom such as a fluorine atom and a chlorine atom; a cyano group; an alkyl group having 1 to 6 carbon atoms, such as a methyl group, an ethyl group, and a propyl group; an alkenyl group having 2 to 6 carbon atoms, such as a vinyl group and an allyl group; an alkyl halide group having 1 to 6 carbon atoms, such as a trifluoromethyl group; a substituted amino group such as a dimethylamino group; an alkoxy group having 1 to 6 carbon atoms, such as a methoxy group, an ethoxy group, and an isopropoxy group; a nitro group; an aryl group such as a phenyl group and a naphthyl group; $—C(=O)—R^4$; $—C(=O)—OR^4$; $—SO_2R^5$; and the like. $R^4$ represents an alkyl group having 1 to 20 carbon atoms, an alkenyl group having 2 to 20 carbon atoms, or a cycloalkyl group having 3 to 12 carbon atoms, and $R^5$ represents an alkyl group having 1 to 20 carbon atoms, an alkenyl group having 2 to 20 carbon atoms, a phenyl group, or a 4-methylphenyl group.

The aromatic ring included in $A^x$ may be substituted with a plurality of identical or different substituents, and two adjacent substituents may be bonded to each other to form a ring. A ring formed by two adjacent substituents may be either a monocyclic ring or a fused polycyclic ring, and may be either an unsaturated ring or a saturated ring.

Note that the number of carbon atoms (i.e., 2 to 30) of the organic group represented by $A^x$ refers to the total number of carbon atoms of the organic group excluding the number of carbon atoms of a substituent.

Examples of the organic group having 2 to 30 carbon atoms represented by $A^x$ (that includes at least one aromatic ring selected from the group consisting of an aromatic hydrocarbon ring and a heteroaromatic ring) include an aromatic hydrocarbon ring group; an aromatic heterocyclic group; an alkyl group having 3 to 30 carbon atoms that includes at least one aromatic ring selected from the group consisting of an aromatic hydrocarbon ring and a heteroaromatic ring; an alkenyl group having 4 to 30 carbon atoms that includes at least one aromatic ring selected from the group consisting of an aromatic hydrocarbon ring and a heteroaromatic ring; an alkynyl group having 4 to 30 carbon atoms that includes at least one aromatic ring selected from the group consisting of an aromatic hydrocarbon ring and a heteroaromatic ring; and the like.

Specific examples of a preferable organic group represented by $A^x$ are given below. Note that the organic group represented by $A^x$ is not limited to the following groups. "—" in the following formulas is a bond from the ring (hereinafter the same).

(1) Aromatic hydrocarbon ring group

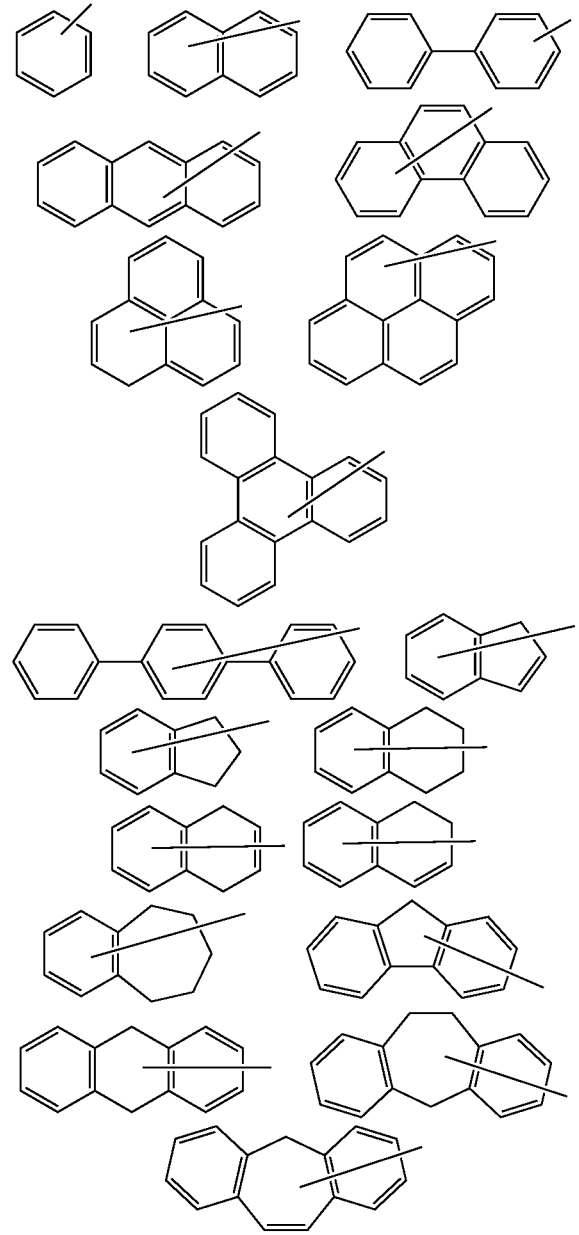

(2) Heteroaromatic ring group

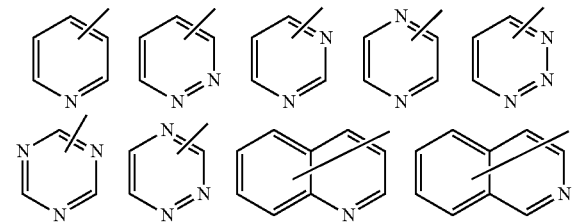

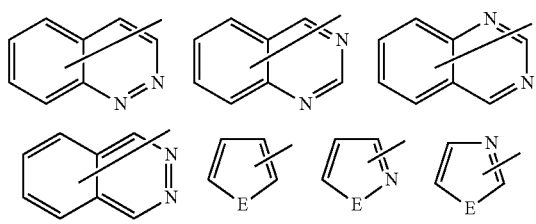

wherein E represents NR[6], an oxygen atom, or a sulfur atom. R[6] represents a hydrogen atom or an alkyl group having 1 to 6 carbon atoms (mentioned above in connection with R[1]).

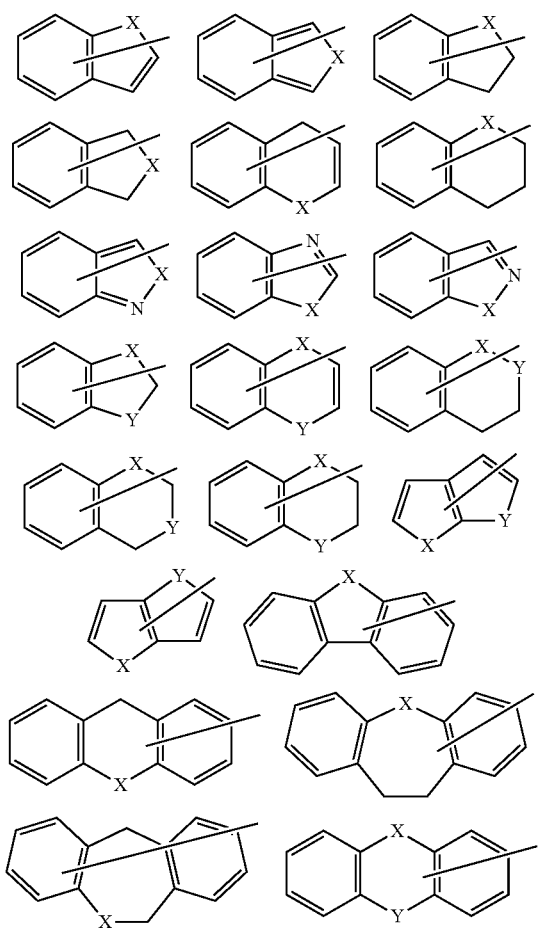

wherein each of X, Y, and Z independently represents NR[6], an oxygen atom, a sulfur atom, —SO—, or —SO$_2$—, provided that a case where two or more oxygen atoms, sulfur atoms, —SO—, or —SO$_2$— are situated at adjacent positions is excluded. R[6] is the same as defined above.

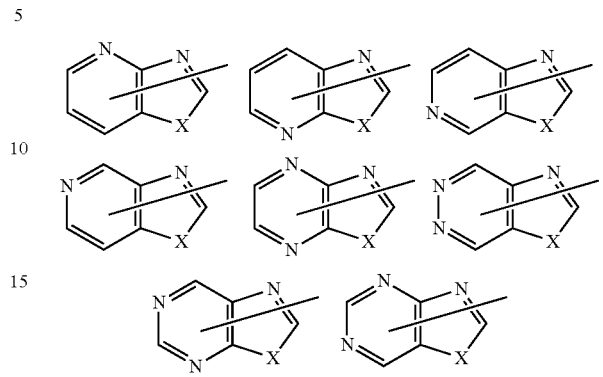

wherein X is the same as defined above.

(3) Alkyl group that includes at least one aromatic ring selected from the group consisting of an aromatic hydrocarbon ring group and a heteroaromatic ring group

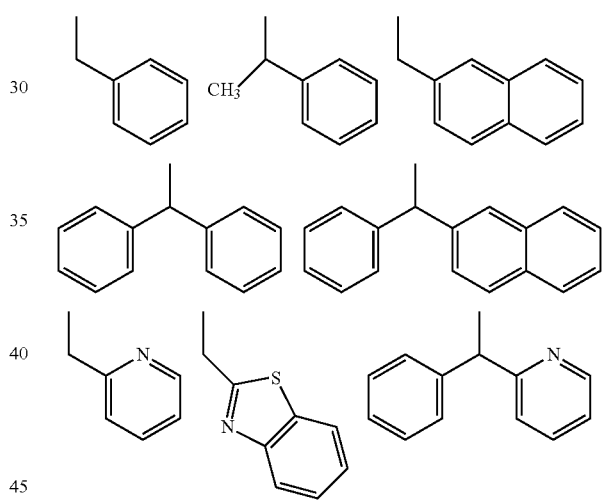

(4) Alkenyl group that includes at least one aromatic ring selected from the group consisting of an aromatic hydrocarbon ring group and a heteroaromatic ring group

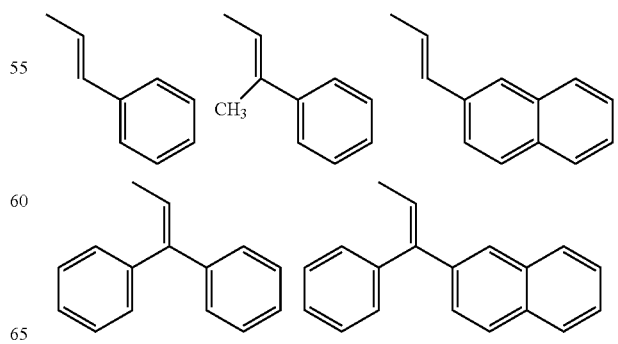

(5) Alkynyl group that includes at least one aromatic ring selected from the group consisting of an aromatic hydrocarbon ring group and a heteroaromatic ring group

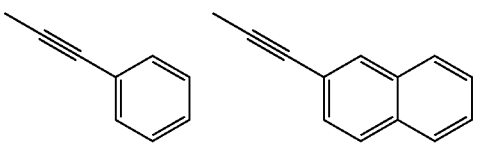

It is preferable that $A^x$ include an aromatic hydrocarbon group having 4 to 30 carbon atoms or a heteroaromatic ring group having 4 to 30 carbon atoms. It is more preferable that $A^x$ include a group among the groups respectively having the following structures.

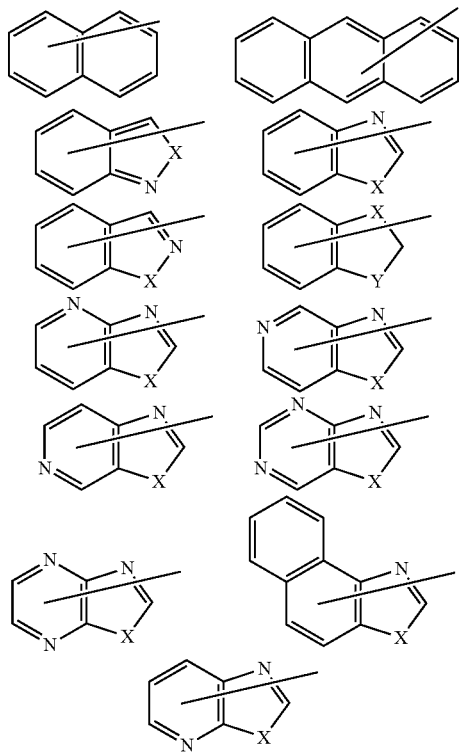

It is still more preferable that $A^x$ include a group among the groups respectively having the following structures.

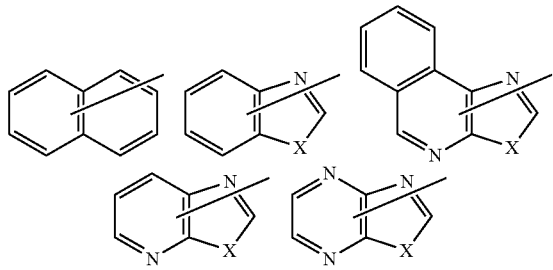

The ring included in $A^x$ may be substituted with a substituent. Examples of the substituent include a halogen atom such as a fluorine atom and a chlorine atom; a cyano group; an alkyl group having 1 to 6 carbon atoms, such as a methyl group, an ethyl group, and a propyl group; an alkenyl group having 2 to 6 carbon atoms, such as a vinyl group and an allyl group; an alkyl halide group having 1 to 6 carbon atoms, such as a trifluoromethyl group; a substituted amino group such as a dimethylamino group; an alkoxy group having 1 to 6 carbon atoms, such as a methoxy group, an ethoxy group, and an isopropoxy group; a nitro group; an aryl group such as a phenyl group and a naphthyl group; $-C(=O)-R^8$; $-C(=O)-OR^8$; $-SO_2R^8$; and the like. Note that $R^8$ represents an alkyl group having 1 to 6 carbon atoms (e.g., methyl group or ethyl group), or an aryl group having 6 to 14 carbon atoms (e.g., phenyl group). Among these, a halogen atom, a cyano group, an alkyl group having 1 to 6 carbon atoms, and an alkoxy group having 1 to 6 carbon atoms are preferable.

The ring included in $A^x$ may be substituted with a plurality of identical or different substituents, and two adjacent substituents may be bonded to each other to form a ring. The ring formed by two adjacent substituents may be either a monocyclic ring or a fused polycyclic ring.

$A^1$ represents a substituted or unsubstituted trivalent aromatic group. The trivalent aromatic group may be a trivalent carbocyclic aromatic group, or may be a trivalent heterocyclic aromatic group. It is preferable that the trivalent aromatic group be a trivalent carbocyclic aromatic group, more preferably a trivalent benzene ring group or a trivalent naphthalene ring group, and still more preferably a group among the trivalent benzene ring group and the trivalent naphthalene ring groups respectively represented by the following formulas, in order to ensure that the intended effects of the invention can be more advantageously achieved.

Note that the substituents $Y^1$ and $Y^2$ are also included in the following formulas so that the bonding state can be easily understood. $Y^1$ and $Y^2$ are the same as defined above (hereinafter the same).

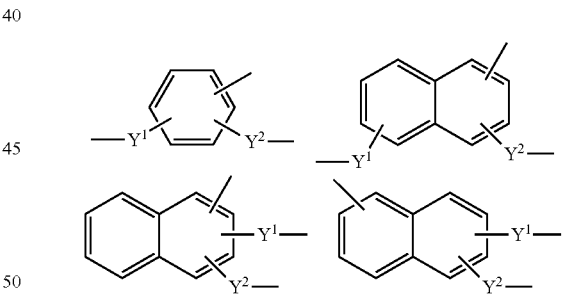

$A^1$ is more preferably a group among the groups respectively represented by the following formulas (A11) to (A25), still more preferably a group among the groups respectively represented by the formulas (A11), (A13), (A15), (A19), and (A23), and particularly preferably the group represented by the formula (A11) or the group represented by the formula (A23).

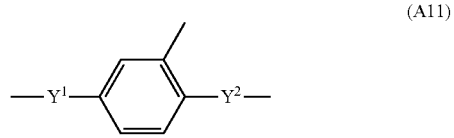

(A11)

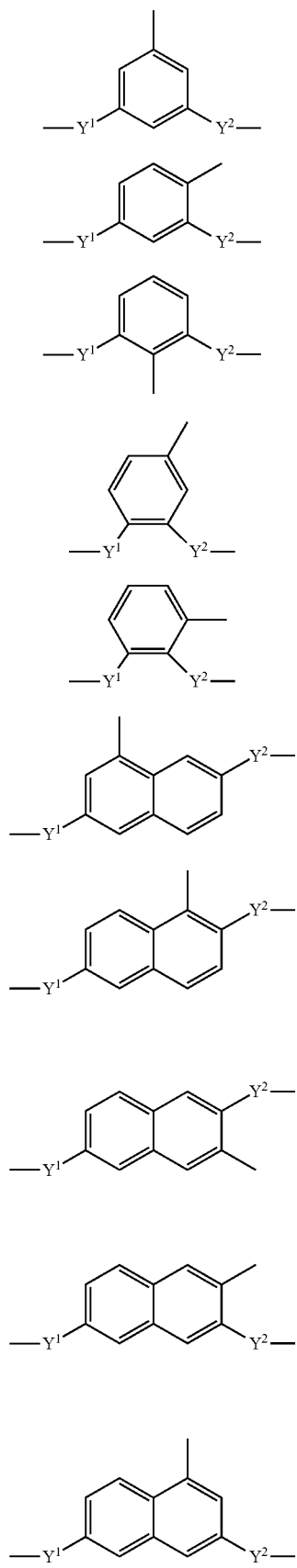

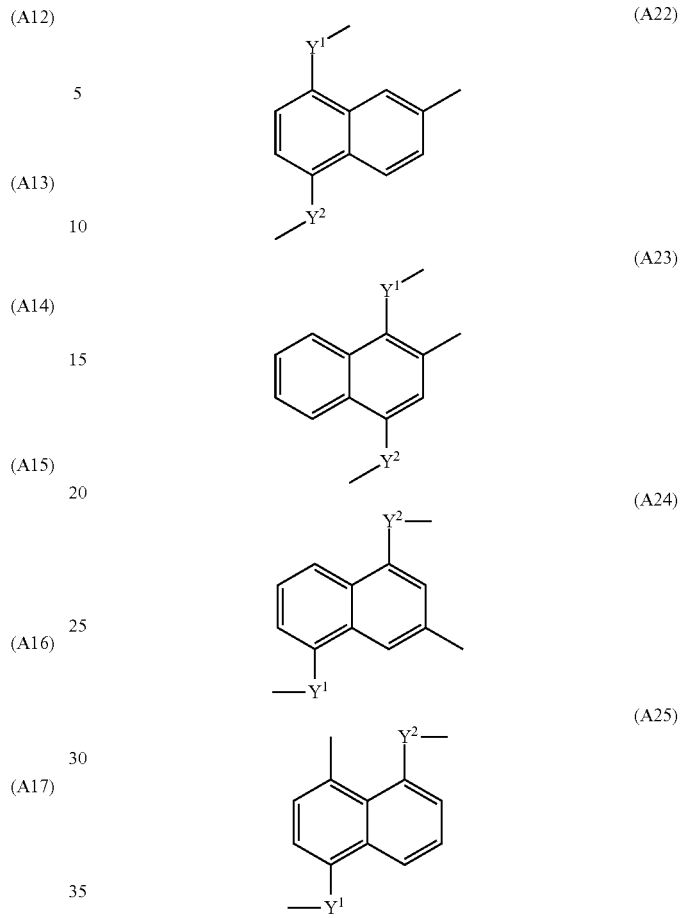

Examples of a substituent that may substitute the trivalent aromatic group represented by $A^1$ include a halogen atom such as a fluorine atom and a chlorine atom; a cyano group; an alkyl group having 1 to 6 carbon atoms, such as a methyl group, an ethyl group, and a propyl group; an alkenyl group having 2 to 6 carbon atoms, such as a vinyl group and an allyl group; an alkyl halide group having 1 to 6 carbon atoms, such as a trifluoromethyl group; a substituted amino group such as a dimethylamino group; an alkoxy group having 1 to 6 carbon atoms, such as a methoxy group, an ethoxy group, and an isopropoxy group; a nitro group; an aryl group such as a phenyl group and a naphthyl group; —C(=O)—$R^7$; —C(=O)—$OR^7$; —$SO_2R^7$; and the like. Note that $R^7$ represents an alkyl group having 1 to 6 carbon atoms (e.g., methyl group or ethyl group), or a substituted or unsubstituted aryl group having 6 to 14 carbon atoms (e.g., phenyl group or 4-methylphenyl group). It is preferable that $A^1$ be unsubstituted.

Each of $A^2$ and $A^3$ independently represents a substituted or unsubstituted divalent alicyclic hydrocarbon group having 3 to 30 carbon atoms.

Examples of the divalent alicyclic hydrocarbon group having 3 to 30 carbon atoms include a cycloalkanediyl group having 3 to 30 carbon atoms, a divalent fused alicyclic group having 10 to 30 carbon atoms, and the like.

Examples of the cycloalkanediyl group having 3 to 30 carbon atoms include a cyclopropanediyl group; a cyclobutanediyl group such as a cyclobutane-1,2-diyl group and a cyclobutane-1,3-diyl group; a cyclopentanediyl group such as a cyclopentane-1,2-diyl group and a cyclopentane-1,3- diyl group; a cyclohexanediyl group such as a cyclohexane-1,2-diyl group, a cyclohexane-1,3-diyl group, and a cyclohexane-1,4-diyl group; a cycloheptanediyl group such as a cycloheptane-1,2-diyl group, a cycloheptane-1,3-diyl group, and a cycloheptane-1,4-diyl group; a cyclooctanediyl group such as a cyclooctane-1,2-diyl group, a cyclooctane-1,3-diyl group, a cyclooctane-1,4-diyl group, and a cyclooctane-1,5-diyl group; a cyclodecanediyl group such as a cyclodecane-1,2-diyl group, a cyclodecane-1,3-diyl group, a cyclodecane-1,4-diyl group, and a cyclodecane-1,5-diyl group; a cyclododecanediyl group such as a cyclododecane-1,2-diyl group, a cyclododecane-1,3-diyl group, a cyclododecane-1,4-diyl group, and a cyclododecane-1,5-diyl group; a cyclotetradecanediyl group such as a cyclotetradecane-1,2-diyl group, a cyclotetradecane-1,3-diyl group, a cyclotetradecane-1,4-diyl group, a cyclotetradecane-1,5-diyl group, and a cyclotetradecane-1,7-diyl group; a cycloeicosanediyl group such as a cycloeicosane-1,2-diyl group and a cycloeicosane-1,10-diyl group; and the like.

Examples of the divalent fused alicyclic group having 10 to 30 carbon atoms include a decalindiyl group such as a decalin-2,5-diyl group and a decalin-2,7-diyl group; an adamantanediyl group such as an adamantane-1,2-diyl group and an adamantane-1,3-diyl group; a bicyclo[2.2.1]heptanediyl group such as a bicyclo[2.2.1]heptane-2,3-diyl group, a bicyclo[2.2.1]heptane-2,5-diyl group, and a bicyclo[2.2.1]heptane-2,6-diyl group; and the like.

These divalent alicyclic hydrocarbon groups may be substituted with a substituent at an arbitrary position. Examples of the substituent include those mentioned above in connection with the aromatic group represented by $A^1$.

$A^2$ and $A^3$ are preferably a divalent alicyclic hydrocarbon group having 3 to 12 carbon atoms, more preferably a cycloalkanediyl group having 3 to 12 carbon atoms, still more preferably a group among the groups respectively represented by the following formulas (A31) to (A34), and particularly preferably the group represented by the formula (A32).

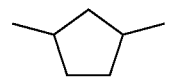
(A31)

(A32)

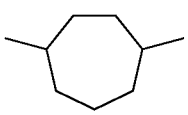
(A33)

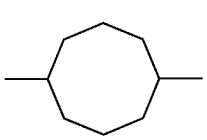
(A34)

The divalent alicyclic hydrocarbon group having 3 to 30 carbon atoms is classified into a cis-stereoisomer and a trans-stereoisomer that differ in the steric configuration of the carbon atoms bonded to $Y^1$ and $Y^3$ (or $Y^2$ and $Y^4$). For example, a cyclohexane-1,4-diyl group is classified into a cis-isomer (A32a) and a trans-isomer (A32b) (see below).

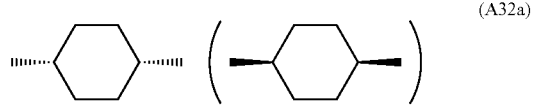
(A32a)

(A32b)

The divalent alicyclic hydrocarbon group having 3 to 30 carbon atoms may be a cis-isomer, a trans-isomer, or a mixture including a cis-isomer and a trans-isomer. Note that it is preferable that the divalent alicyclic hydrocarbon group having 3 to 30 carbon atoms be a trans-isomer or a cis-isomer, and more preferably a trans-isomer, since an excellent alignment capability can be obtained.

Each of $A^4$ and $A^5$ independently represents a substituted or unsubstituted divalent aromatic group having 4 to 30 carbon atoms.

The aromatic group represented by $A^4$ and $A^5$ may be a monocyclic aromatic group, or may be a polycyclic aromatic group.

Specific examples of a preferable aromatic group represented by $A^4$ and $A^5$ include the groups respectively represented by the following formulas.

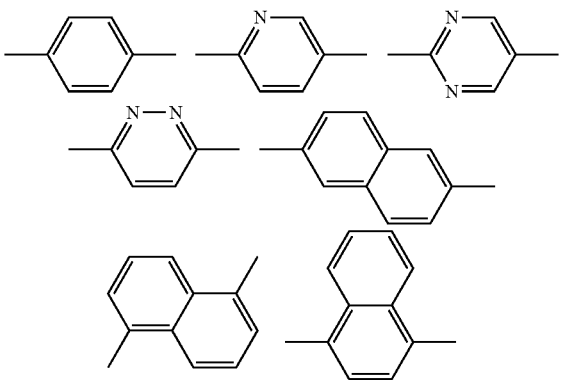

The divalent aromatic group represented by $A^4$ and $A^5$ may be substituted with a substituent at an arbitrary position. Examples of the substituent include a halogen atom, a cyano group, a hydroxyl group, an alkyl group having 1 to 6 carbon atoms, an alkoxy group having 1 to 6 carbon atoms, a nitro group, a —C(=O)—OR$^9$ group, and the like. Note that R$^9$ is an alkyl group having 1 to 6 carbon atoms. Among these, a halogen atom, an alkyl group having 1 to 6 carbon atoms, and an alkoxy group having 1 to 6 carbon atoms are preferable as the substituent. A fluorine atom is preferable as the halogen atom. A methyl group, an ethyl group, and a propyl group are preferable as the alkyl group having 1 to 6 carbon atoms. A methoxy group and an ethoxy group are preferable as the alkoxy group having 1 to 6 carbon atoms.

It is preferable that each of $A^4$ and $A^5$ be independently a group among the groups respectively represented by the following formulas (A41), (A42), and (A43) that are optionally substituted with a substituent, and particularly preferably the group represented by the formula (A41) that is optionally substituted with a substituent, in order to ensure that the intended effects of the invention can be more advantageously achieved.

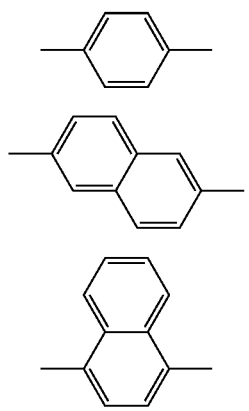

$Q^1$ represents a hydrogen atom, or a substituted or unsubstituted alkyl group having 1 to 6 carbon atoms.

Examples of the substituted or unsubstituted alkyl group having 1 to 6 carbon atoms include those mentioned above in connection with $R^1$.

It is preferable that $Q^1$ be a hydrogen atom or an alkyl group having 1 to 6 carbon atoms, and more preferably a hydrogen atom or a methyl group.

Each of m and n independently represents 0 or 1. It is preferable that both m and n be 0.

The polymerizable compound (I) according to one embodiment of the invention may be produced using the following methods, for example.

Production Method 1

The polymerizable compound (I) wherein $Y^a$ is the group shown below (i.e., polymerizable compound (Ia)) may be produced as described below, for example.

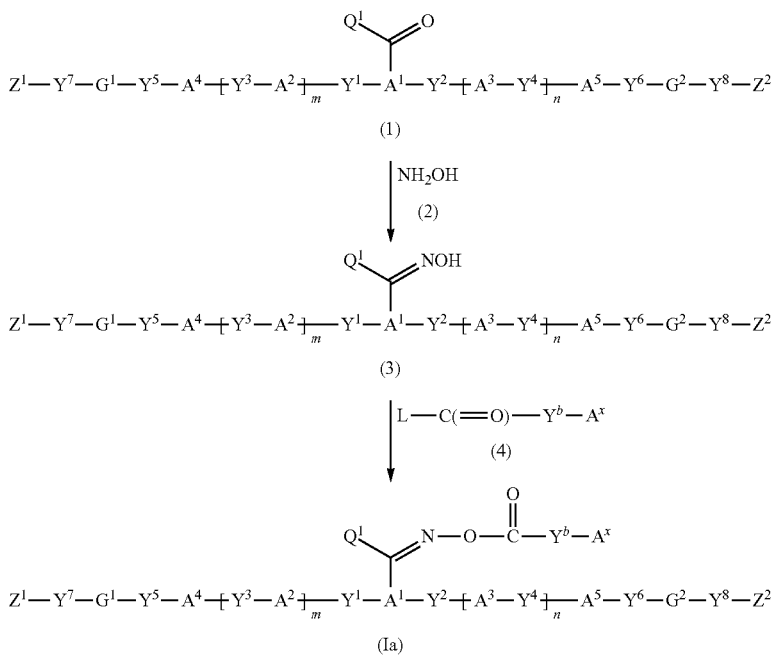

wherein $Y^1$ to $Y^8$, $Y^a$, $G^1$, $G^2$, $Z^1$, $Z^2$, $A^x$, $A^1$~$A^5$, $Q^1$, m, and n are the same as defined above, $Y^b$ represents a group included in —O—C(=O)—$Y^b$— that corresponds to $Y^a$, and L represents a leaving group (e.g., halogen atom (e.g., chlorine atom or bromine atom), methanesulfonyloxy group, or p-toluenesulfonyloxy group) (hereinafter the same).

Specifically, the target polymerizable compound (Ia) according to one embodiment of the invention can be produced by reacting hydroxylamine represented by the formula (2) (compound (2)) with the carbonyl compound represented by the formula (1) (carbonyl compound (1)) in a molar ratio (compound (2):carbonyl compound (1)) of 1:1 to 2:1 to obtain the compound represented by the formula (3) (compound (3)), and reacting the compound (3) with the compound represented by the formula (4) (compound (4)) in a molar ratio (compound (3):compound (4)) of 1:1 to 1:2. Note that hydroxylamine may be used in the form of a hydrochloride.

The reaction that synthesizes the compound (3) may be effected using an acid catalyst such as an organic acid (e.g., (±)-10-camphorsulfonic acid or p-toluenesulfonic acid), or an inorganic acid (e.g., hydrochloric acid or sulfuric acid). The addition of the acid catalyst may reduce the reaction time, and improve the yield. The acid catalyst is normally added in an amount of 0.001 to 1 mol based on 1 mol of the carbonyl compound (1). The acid catalyst may be added directly, or a solution prepared by dissolving the acid catalyst in an appropriate solvent may be added.

A solvent used for the above reaction is not particularly limited as long as the solvent is inert to the reaction. Examples of the solvent include an alcohol-based solvent such as methyl alcohol, ethyl alcohol, n-propyl alcohol, isopropyl alcohol, n-butyl alcohol, isobutyl alcohol, sec-butyl alcohol, and t-butyl alcohol; an ether-based solvent such as diethyl ether, tetrahydrofuran, 1,2-dimethoxyethane, 1,4-dioxane, and cyclopentyl methyl ether; an ester-based solvent such as ethyl acetate, propyl acetate, and methyl propionate; an aromatic hydrocarbon-based solvent such as benzene, toluene, and xylene; an aliphatic hydrocarbon-based solvent such as n-pentane, n-hexane, and n-heptane; an amide-based solvent such as N,N-dimethylformamide, N-methylpyrrolidone, and hexamethylphosphoric acid triamide; a sulfur-containing solvent such as dimethyl sulfoxide and sulfolane; a mixed solvent including two or more solvents among these solvents; and the like.

Among these, an alcohol-based solvent, an ether-based solvent, and a mixed solvent including an alcohol-based solvent and an ether-based solvent are preferable.

The solvent may be used in an appropriate amount taking account of the type of each compound, the reaction scale, and the like. The solvent is normally used in an amount of 1 to 100 g per gram of the compound (2).

The reaction proceeds smoothly when the reaction temperature is set within the range from -10° C. to the boiling point of the solvent. The reaction time is selected taking account of the reaction scale, but is normally set to several minutes to several hours.

The compound (4) is reacted with the compound (3) to obtain the target product. This reaction is preferably effected in the presence of a base such as triethylamine, diisopropylethylamine, pyridine, or 4-(dimethylamino)pyridine.

A solvent used for this reaction is not particularly limited as long as the solvent is inert to the reaction. Examples of the solvent include those mentioned above in connection with the solvent used when synthesizing the compound (3). It is preferable to use an ether-based solvent.

The reaction proceeds smoothly when the reaction temperature is set within the range from -10° C. to the boiling point of the solvent. The reaction time is selected taking account of the reaction scale, but is normally set to several minutes to several hours.

Production Method 2

The polymerizable compound (Ia) wherein $Y^b$ is —NH— (polymerizable compound (Ia')) may be produced substantially in the same manner as in the production method 1, except that a compound (4') is used instead of the compound (4) (see below).

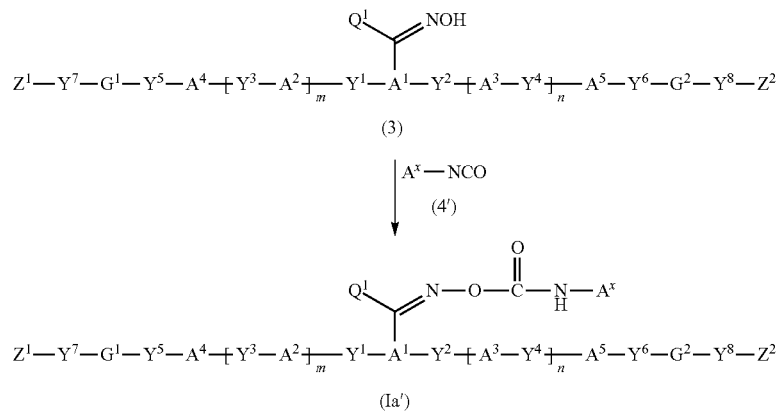

Production Method 3

The polymerizable compound (I) wherein $Y^a$ is —O— (polymerizable compound (Ib)) may be produced as described below, for example.

The reaction may be effected under substantially the same conditions as those employed when reacting the compound (1) and the compound (2).

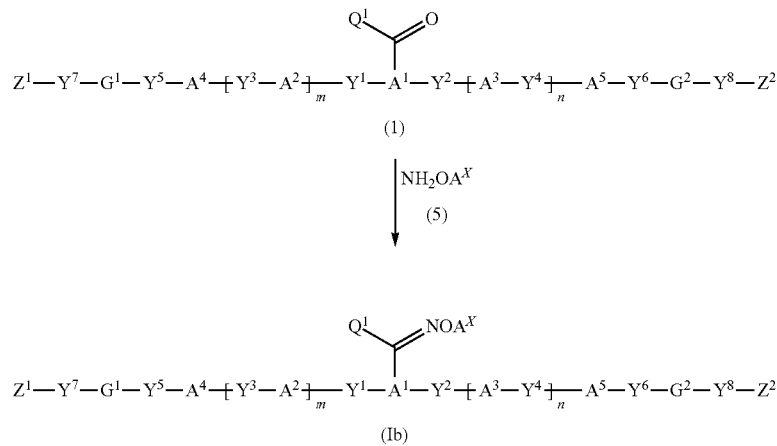

Production Method 4

The polymerizable compound (I) wherein $Y^a$ is $-C(=O)-Y^c-$ (polymerizable compound (Ic)) may be produced as described below, for example. Note that $Y^c$ represents a group included in $-C(=O)-Y^c-$ that corresponds to $Y^a$.

Specifically, ammonia is reacted with the compound (1) to obtain the compound represented by the formula (6) (compound (6)), and the compound represented by the formula (7) (compound (7)) is reacted with the compound (6) to obtain the target polymerizable compound (Ic).

The reaction may be effected under substantially the same conditions as those employed when reacting the compound (3) and the compound (4).

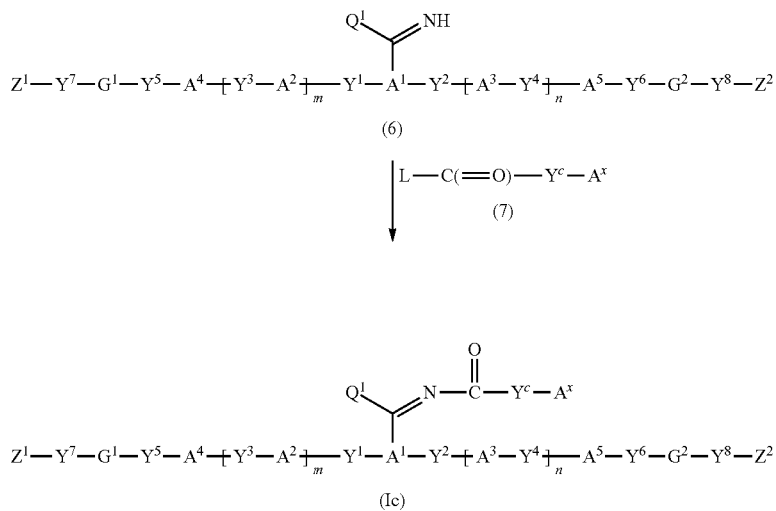

The carbonyl compound (1) may be produced by appropriately bonding and modifying a plurality of known compounds having a desired structure by arbitrarily combining an ether linkage (—O—)-forming reaction, an ester linkage (—C(=O)—O— or —O—C(=O)—)-forming reaction, a carbonate linkage (—O—C(=O)—O—)-forming reaction, and an amide linkage (—C(=O)—NH— or —NH—C(=O)—)-forming reaction.

An ether linkage may be formed as described below.

(i) A compound represented by D1-hal (wherein hal represents a halogen atom (hereinafter the same)) and a compound represented by D2-OMet (wherein Met represents an alkali metal (mainly sodium) (hereinafter the same)) are mixed and condensed (Williamson synthesis). Note that D1 and D2 represent an arbitrary organic group (hereinafter the same).

(ii) A compound represented by D1-hal and a compound represented by D2-OH are mixed and condensed in the presence of a base (e.g., sodium hydroxide or potassium hydroxide).

(iii) A compound represented by D1-J (wherein J represents an epoxy group) and a compound represented by D2-OH are mixed and condensed in the presence of a base (e.g., sodium hydroxide or potassium hydroxide).

(iv) A compound represented by D1-OFN (wherein OFN represents a group that includes an unsaturated bond) and a compound represented by D2-OMet are mixed and subjected to an addition reaction in the presence of a base (e.g., sodium hydroxide or potassium hydroxide).

(v) A compound represented by D1-hal and a compound represented by D2-OMet are mixed and condensed in the presence of copper or cuprous chloride (Ullmann condensation).

An ester linkage and an amide linkage may be formed as described below.

(vi) A compound represented by D1-COOH and a compound represented by D2-OH or D2-NH$_2$ are subjected to dehydration and condensation in the presence of a dehydration-condensation agent (e.g., N,N-dicyclohexylcarbodiimide).

(vii) A compound represented by D1-COOH is reacted with a halogenating agent to obtain a compound represented by D1-CO-hal, and the compound represented by D1-CO-hal is reacted with a compound represented by D2-OH or D2-NH$_2$ in the presence of a base.

(viii) A compound represented by D1-COOH is reacted with an acid anhydride to obtain a mixed acid anhydride, and the mixed acid anhydride is reacted with a compound represented by D2-OH or D2-NH$_2$.

(ix) A compound represented by D1-COOH and a compound represented by D2-OH or D2-NH$_2$ are subjected to dehydration and condensation in the presence of an acid catalyst or a base catalyst.

More specifically, the carbonyl compound (1) may be produced using the following method (see the following reaction formula).

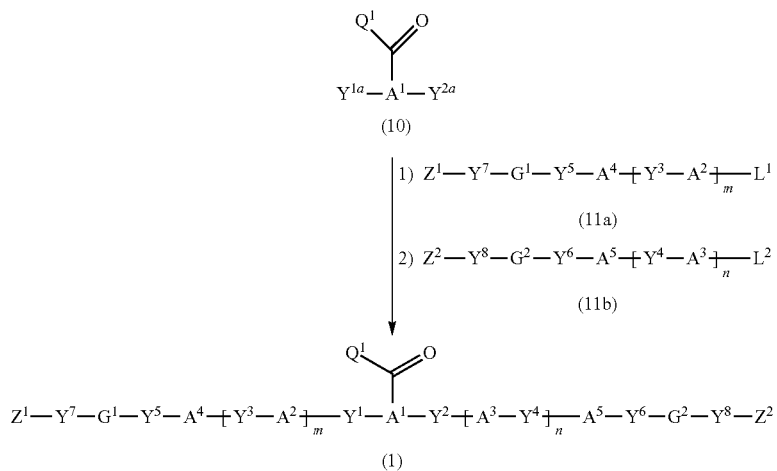

wherein $L^1$ and $L^2$ represent a leaving group (e.g., hydroxyl group, halogen atom, methanesulfonyloxy group, or p-toluenesulfonyloxy group), —$Y^{1a}$ represents a group that reacts with -$L^1$ to form —$Y^1$—, and —$Y^{2a}$ represents a group that reacts with -$L^2$ to form —$Y^2$—.

Specifically, the carbonyl compound (1) according to one embodiment of the invention may be produced by sequentially reacting the compound represented by the formula (11a) and the compound represented by the formula (11b) with the compound represented by the formula (10) using an ether linkage (—O—)-forming reaction, an ester linkage (—C(=O)—O— or —O—C(=O)—)-forming reaction, or a carbonate linkage (—O—C(=O)—O—)-forming reaction known in the art.

A compound (1') in which $Y^1$ is a group represented by —C(=O)—O—, and the group represented by $Z^2$—$Y^8$-$G^2$-$Y^6$-$A^5$-$(Y^4$-$A^3)_n$-$Y^2$— is identical to the group represented by $Z^1$—$Y^7$-$G^1$-$Y^5$-$A^4$-$(Y^3$-$A^2)_m$-$Y^1$- may be produced as shown below.

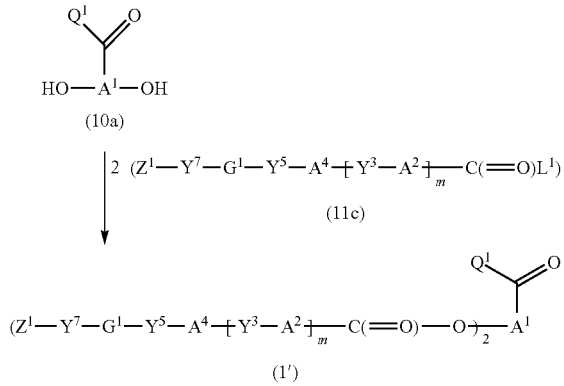

Specifically, the dihydroxy compound represented by the formula (10a) (compound (10a)) is reacted with the compound represented by the formula (11c) (compound (11c)) in a molar ratio (compound (10a):compound (11c)) of 1:2 to 1:4 (preferably 1:2 to 1:3) to produce the target compound (1') with high selectivity in high yield.

When the compound (11c) is the compound (carboxylic acid) represented by the formula (11c) wherein $L^1$ is a hydroxyl group, the target product may be obtained by effecting the reaction in the presence of a dehydration-condensation agent (e.g., 1-ethyl-3-(3-dimethylaminopropyl)carbodiimide hydrochloride or dicyclohexylcarbodiimide).

The dehydration-condensation agent is normally used in an amount of 1 to 3 mol based on 1 mol of the compound (11c).

When the compound (11c) is the compound (carboxylic acid) represented by the formula (11c) wherein $L^1$ is a hydroxyl group, the target product may also be obtained by effecting the reaction in the presence of a sulfonyl halide (e.g., methanesulfonyl chloride or p-toluenesulfonyl chloride) and a base (e.g., triethylamine, diisopropylethylamine, pyridine, or 4-(dimethylamino)pyridine).

The sulfonyl halide is normally used in an amount of 1 to 3 mol based on 1 mol of the compound (11c).

The base is normally used in an amount of 1 to 3 mol based on 1 mol of the compound (11c).

In this case, the compound (mixed acid anhydride) represented by the formula (11c) wherein $L^1$ is a sulfonyloxy group may be isolated, and subjected to the subsequent reaction.

When the compound (11c) is the compound (acid halide) represented by the formula (11c) wherein $L^1$ is a halogen atom, the target product may be obtained by effecting the reaction in the presence of a base.

Examples of the base include an organic base such as triethylamine and pyridine; and an inorganic base such as sodium hydroxide, sodium carbonate, and sodium hydrogen carbonate.

The base is normally used in an amount of 1 to 3 mol based on 1 mol of the compound (11c).

Examples of the solvent used for the above reaction include a chlorine-based solvent such as chloroform and methylene chloride; an amide-based solvent such as N-methylpyrrolidone, N,N-dimethylformamide, N,N-dimethylacetamide, and hexamethylphosphoric triamide; an ether-based solvent such as 1,4-dioxane, cyclopentyl methyl ether, tetrahydrofuran, tetrahydropyran, and 1,3-dioxolane; a sulfur-containing solvent such as dimethyl sulfoxide and sulfolane; an aromatic hydrocarbon-based solvent such as benzene, toluene, and xylene; an aliphatic hydrocarbon-based solvent such as n-pentane, n-hexane, and n-octane; an alicyclic hydrocarbon-based solvent such as cyclopentane and cyclohexane; a mixed solvent including two or more solvents among these solvents; and the like.

The solvent may be used in an appropriate amount taking account of the type of each compound, the reaction scale, and the like. The solvent is normally used in an amount of 1 to 50 g per gram of the hydroxy compound (10a).

Many of the compounds (10a) are known compounds, and may be produced using a known method.

For example, the compound (10a) may be produced using the following method (see the following reaction formula) (see WO2009/042544 and The Journal of Organic Chemistry, 2011, 76, 8082-8087). A commercially available product may be used as the compound (10a) either directly or after purification.

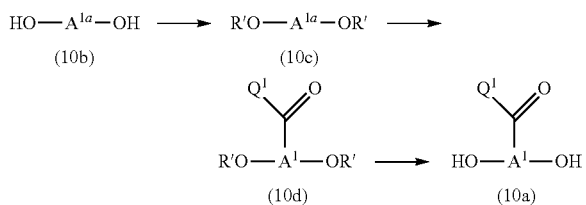

wherein $A^{1a}$ represents a divalent aromatic group that forms $A^1$ through formylation or acylation, and R' represents a protecting group for a hydroxyl group, such as an alkyl group having 1 to 6 carbon atoms (e.g., methyl group or ethyl group), or an alkoxyalkyl group having 2 to 6 carbon atoms (e.g., methoxymethyl group).

Specifically, the target compound (10a) can be produced by alkylating the hydroxyl groups of the dihydroxy compound represented by the formula (10b) (e.g., 1,4-dihydroxybenzene or 1,4-dihydroxynaphthalene) to obtain the compound represented by the formula (10c), effecting formylation or acylation at the ortho position with respect to the OR' group using a known method to obtain the compound represented by the formula (10d), and deprotecting (dealkylating) the compound represented by the formula (10d).

A commercially available product may be used as the compound (10a) either directly or after purification.

Most of the compounds (11c) are known compounds. The compound (11c) may be produced by appropriately bonding and modifying a plurality of known compounds having a desired structure by arbitrarily combining an ether linkage (—O—)-forming reaction, an ester linkage (—C(=O)—O— or —O—C(=O)—)-forming reaction, a carbonate linkage (—O—C(=O)—O—)-forming reaction, and an amide linkage (—C(=O)—NH— or —NH—C(=O)—)-forming reaction.

For example, when the compound (11c) is a compound represented by the following formula (11d) (compound (11d)), the compound (11d) may be produced as described below using a dicarboxylic acid represented by the formula (12) (compound (12)).

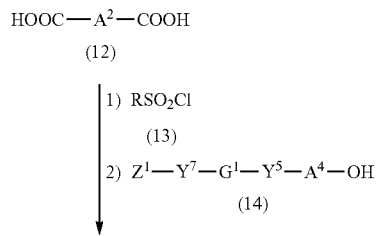

-continued

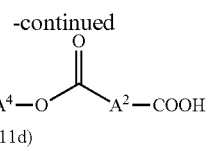

wherein R represents an alkyl group (e.g., methyl group or ethyl group) or a substituted or unsubstituted aryl group (e.g., phenyl group or p-methylphenyl group).

Specifically, the sulfonyl chloride represented by the formula (13) is reacted with the compound (12) in the presence of a base (e.g., triethylamine or 4-(dimethylamino) pyridine).

The compound (14) and a base (e.g., triethylamine or 4-(dimethylamino)pyridine) are added to the reaction mixture to effect a reaction.

The sulfonyl chloride is normally used in an amount of 0.5 to 0.7 equivalents based on 1 equivalent of the compound (12).

The compound (14) is normally used in an amount of 0.5 to 0.6 equivalents based on 1 equivalent of the compound (12).

The base is normally used in an amount of 0.5 to 0.7 equivalents based on 1 equivalent of the compound (12).

The reaction temperature is set to 20 to 30° C. The reaction time is determined taking account of the reaction scale and the like, but is normally set to several minutes to several hours.

Examples of a solvent used for the above reaction include those mentioned above in connection with the solvent that may be used when producing the compound (1'). It is preferable to use an ether as the solvent.

The solvent may be used in an appropriate amount taking account of the type of each compound, the reaction scale, and the like. The solvent is normally used in an amount of 1 to 50 g per gram of the compound (12).

The target product is isolated by performing a post-treatment operation normally employed in synthetic organic chemistry after completion of the reaction, optionally followed by a known purification-separation means such as column chromatography, recrystallization, or distillation.

The structure of the target product may be identified by measurement/elemental analysis (e.g., NMR spectrometry, IR spectrometry, or mass spectrometry), and the like.

2) Polymerizable Composition

A polymerizable composition according to one embodiment of the invention includes the polymerizable compound according to one embodiment of the invention, and an initiator. The initiator is used in order to more efficiently polymerize the polymerizable composition according to one embodiment of the invention.

The initiator may be appropriately selected taking account of the type of the polymerizable group included in the polymerizable compound. For example, a radical initiator may be used when the polymerizable group is a radically polymerizable group, an anionic initiator may be used when the polymerizable group is an anionically polymerizable group, and a cationic initiator may be used when the polymerizable group is a cationically polymerizable group.

Examples of the radical initiator include a thermal radical generator that is a compound that generates active species that initiate the polymerization of the polymerizable compound upon heating, and a photo-radical generator that is a compound that generates active species that initiate the polymerization of the polymerizable compound upon exposure to exposure light (e.g., visible light, ultraviolet rays (e.g., i-line), deep ultraviolet rays, electron beams, or X-rays). It is preferable to use the photo-radical generator.

Examples of the photo-radical generator include an acetophenone-based compound, a biimidazole-based compound, a triazine-based compound, an O-acyloxime-based compound, an onium salt-based compound, a benzoin-based compound, a benzophenone-based compound, an a-diketone-based compound, a polynuclear quinone-based compound, a xanthone-based compound, a diazo-based compound, an imide sulfonate-based compound, and the like. These compounds generate either or both of active radicals and an active acid upon exposure. These photo-radical generators may be used either alone or in combination.

Specific examples of the acetophenone-based compound include 2-hydroxy-2-methyl-1-phenylpropan-1-one, 2-methyl-1-[4-(methylthio)phenyl]-2-morpholinopropan-1-one, 2-benzyl-2-dimethylamino-1-(4-morpholinophenyl)butan-1-one, 1-hydroxycyclohexyl phenyl ketone, 2,2-dimethoxy-1,2-diphenylethan-1-one, 1,2-octanedione, 2-benzyl-2-dimethylamino-4'-morpholinobutyrophenone, and the like.

Specific examples of the biimidazole-based compound include 2,2'-bis(2-chlorophenyl)-4,4',5,5'-tetrakis(4-ethoxycarbonylphenyl)-1,2'-biimidazole, 2,2'-bis(2-bromophenyl)-4,4',5,5'-tetrakis(4-ethoxycarbonylphenyl)-1,2'-biimidazole, 2,2'-bis(2-chlorophenyl)-4,4',5,5'-tetraphenyl-1,2'-biimidazole, 2,2'-bis(2,4-dichlorophenyl)-4,4',5,5'-tetraphenyl-1,2'-biimidazole, 2,2'-bis(2,4,6-trichlorophenyl)-4,4',5,5'-tetraphenyl-1,2'-biimidazole, 2,2'-bis(2-bromophenyl)-4,4',5,5'-tetraphenyl-1,2'-biimidazole, 2,2'-bis(2,4-dibromophenyl)-4,4',5,5'-tetraphenyl-1,2'-biimidazole, 2,2'-bis(2,4,6-tribromophenyl)-4,4',5,5'-tetraphenyl-1,2'-biimidazole, and the like.

When using a biimidazole-based compound as a photoinitiator, it is preferable to use a hydrogen donor in combination with the biimidazole-based compound in order to further improve sensitivity.

The term "hydrogen donor" used herein refers to a compound that can donate a hydrogen atom to radicals generated by the biimidazole-based compound upon exposure. A mercaptan-based compound (see below), an amine-based compound (see below), and the like are preferable as the hydrogen donor.

Examples of the mercaptan-based compound include 2-mercaptobenzothiazole, 2-mercaptobenzoxazole, 2-mercaptobenzimidazole, 2,5-dimercapto-1,3,4-thiadiazole, 2-mercapto-2,5-dimethylaminopyridine, and the like. Examples of the amine-based compound include 4,4'-bis(dimethylamino)benzophenone, 4,4'-bis(diethylamino)benzophenone, 4-diethylaminoacetophenone, 4-dimethylaminopropiophenone, ethyl-4-dimethylaminobenzoate, 4-dimethylaminobenzoic acid, 4-dimethylaminobenzonitrile, and the like.

Specific examples of the triazine-based compound include a triazine-based compound that includes a halomethyl group, such as 2,4,6-tris(trichloromethyl)-s-triazine, 2-methyl-4,6-bis(trichloromethyl)-s-triazine, 2-[2-(5-methylfuran-2-yl)ethenyl]-4,6-bis(trichloromethyl)-s-triazine, 2-[2-(furan-2-yl)ethenyl]-4,6-bis(trichloromethyl)-s-triazine, 2-[2-(4-diethylamino-2-methylphenyl)ethenyl]-4,6-bis(trichloromethyl)-s-triazine, 2-[2-(3,4-dimethoxyphenyl)ethenyl]-4,6-bis(trichloromethyl)-s-triazine, 2-(4-methoxyphenyl)-4,6-bis(trichloromethyl)-s-triazine, 2-(4-ethoxystyryl)-4,6-bis(trichloromethyl)-s-triazine, and 2-(4-n-butoxyphenyl)-4,6-bis(trichloromethyl)-s-triazine.

Specific examples of the O-acyloxime-based compound include 1-[4-(phenylthio)phenyl]-heptane-1,2-dione-2-(O-benzoyloxime), 1-[4-(phenylthio)phenyl]-octane-1,2-dione-2-(O-benzoyloxime), 1-[4-(benzoyl)phenyl]-octane-1,2-dione-2-(O-benzoyloxime), 1-[9-ethyl-6-(2-methylbenzoyl)-9H-carbazol-3-yl]-ethanone-1-(O-acetyloxime), 1-[9-ethyl-6-(3-methylbenzoyl)-9H-carbazol-3-yl]-ethanone-1-(O-acetyloxime), 1-(9-ethyl-6-benzoyl-9h-carbazol-3-yl)-ethanone-1-(O-acetyloxime), ethanone-1-[9-ethyl-6-(2-methyl-4-tetrahydrofuranylbenzoyl)-9H-carbazol-3-yl]-1-(O-acetyloxime), ethanone-1-[9-ethyl-6-(2-methyl-4-tetrahydropyranylbenzoyl)-9H-carbazol-3-yl]-1-(O-acetyloxime), ethanone-1-[9-ethyl-6-(2-methyl-5-tetrahydrofuranylbenzoyl)-9H-carbazol-3-yl]-1-(O-acetyloxime), ethanone-1-[9-ethyl-6-(2-methyl-5-tetrahydropyranylbenzoyl)-9H-carbazol-3-yl]-1-(O-acetyloxime), ethanone-1-[9-ethyl-6-{2-methyl-4-(2,2-dimethyl-1,3-dioxolanyl)benzoyl}-9H-carbazol-3-yl]-1-(O-acetyloxime), ethanone-1-[9-ethyl-6-(2-methyl-4-tetrahydrofuranylmethoxybenzoyl)-9H-carbazol-3-yl]-1-(O-acetyloxime), ethanone-1-[9-ethyl-6-(2-methyl-4-tetrahydropyranylmethoxybenzoyl)-9H-carbazol-3-yl]-1-(O-acetyloxime), ethanone-1-[9-ethyl-6-(2-methyl-5-tetrahydrofuranylmethoxybenzoyl)-9H-carbazol-3-yl]-1-(O-acetyloxime), ethanone-1-[9-ethyl-6-(2-methylbenzoyl)-9H-carbazol-3-yl]-1-(O-acetyloxime), ethanone-1-[9-ethyl-6-(2-methyl-5-tetrahydropyranylmethoxybenzoyl)-9H-carbazol-3-yl]-1-(O-acetyloxime), ethanone-1-[9-ethyl-6-{2-methyl-4-(2,2-dimethyl-1,3-dioxolanyl)methoxybenzoyl}-9H-carbazol-3-yl]-1-(O-acetyloxime), and the like.

A commercially available product may be used directly as the photo-radical generator. Specific examples of a commercially available photo-radical generator include Irgacure 907, Irgacure 184, Irgacure 369, Irgacure 651, Irgacure 819, and Irgacure 907, Irgacure OXE02 (manufactured by BASF); Adekaoptomer N1919 (manufactured by Adeka Corporation); and the like.

Examples of the anionic initiator include an alkyllithium compound; a monolithium salt or a monosodium salt of biphenyl, naphthalene, pyrene, and the like; a polyfunctional initiator such as a dilithium salt and a trilithium salt; and the like.

Examples of the cationic initiator include a proton acid such as sulfuric acid, phosphoric acid, perchloric acid, and trifluoromethanesulfonic acid; a Lewis acid such as boron trifluoride, aluminum chloride, titanium tetrachloride, and tin tetrachloride; an aromatic onium salt or a combination of an aromatic onium salt and a reducing agent; and the like.

These initiators may be used either alone or in combination.

The initiator is normally added to the polymerizable composition according to one embodiment of the invention in a ratio of 0.1 to 30 parts by weight, and preferably 0.5 to 10 parts by weight, based on 100 parts by weight of the polymerizable compound.

It is preferable to add a surfactant to the polymerizable composition according to one embodiment of the invention in order to adjust the surface tension of the polymerizable composition. The surfactant is not particularly limited. A nonionic surfactant is normally preferable as the surfactant. A commercially available product may be used as the nonionic surfactant. Examples of a commercially available product that may be used as the nonionic surfactant include an oligomer having a molecular weight of about several thousand (e.g., "KH-40" manufactured by AGC Seimi Chemical Co., Ltd.), and the like. The surfactant is normally added to the polymerizable composition according to one embodiment of the invention in a ratio of 0.01 to 10 parts by weight, and preferably 0.1 to 2 parts by weight, based on 100 parts by weight of the polymerizable compound.

The polymerizable composition according to one embodiment of the invention may further include an additional additive such as an additional copolymerizable monomer (described later), a metal, a metal complex, a dye, a pigment, a fluorescent material, a phosphorescent material, a leveling agent, a thixotropic agent, a gelling agent, a polysaccharide, a UV absorber, an IR (infrared) absorber, an antioxidant, an ion-exchange resin, and a metal oxide (e.g., titanium oxide). Each additive is normally added to the polymerizable composition according to one embodiment of the invention in a ratio of 0.1 to 20 parts by weight based on 100 parts by weight of the polymerizable compound.

The polymerizable composition according to one embodiment of the invention may be prepared by mixing and dissolving given amounts of the polymerizable compound according to one embodiment of the invention, the initiator, and an optional additive in an appropriate organic solvent.

Examples of the organic solvent include a ketone such as cyclopentanone, cyclohexanone, and methyl ethyl ketone; an acetate such as butyl acetate and amyl acetate; a halogenated hydrocarbon such as chloroform, dichloromethane, and dichloroethane; an ether such as 1,4-dioxane, cyclopentyl methyl ether, tetrahydrofuran, tetrahydropyran, and 1,3-dioxolane; and the like.

The polymerizable composition thus obtained is useful as a material for producing a polymer according to one embodiment of the invention, or producing an optically anisotropic product according to one embodiment of the invention (described below).

3) Polymer

A polymer according to one embodiment of the invention is (1) a polymer obtained by polymerizing the polymerizable compound according to one embodiment of the invention, or (2) a polymer obtained by polymerizing the polymerizable composition according to one embodiment of the invention.

The term "polymerization" used herein refers to a chemical reaction in a broad sense including a normal polymerization reaction and a cross-linking reaction.

(1) Polymer Obtained by Polymerizing Polymerizable Compound

The polymer obtained by polymerizing the polymerizable compound according to one embodiment of the invention may be a homopolymer of the polymerizable compound according to one embodiment of the invention, a copolymer of two or more types of the polymerizable compounds according to one embodiment of the invention, or a copolymer of the polymerizable compound according to one embodiment of the invention and an additional copolymerizable monomer.

Examples of the additional copolymerizable monomer include a commercially available product such as LC-242 (manufactured by BASF), the compounds disclosed in JP-A-2007-002208, JP-A-2009-173893, JP-A-2009-274984, JP-A-2010-030979, JP-A-2010-031223, JP-A-2011-006360, PCT/JP2012/060011 (WO2012/141245), PCT/JP2012/061321 (WO2012/147904), PCT/JP2012/064111 (WO2012/169424), PCT/JP2012/065202 (WO2012/176679), and PCT/2012/067906, and the like.

Further examples of the additional copolymerizable monomer include 4'-methoxyphenyl 4-(2-methacryloyloxyethyloxy)benzoate, biphenyl 4-(6-methacryloyloxyhexyloxy)benzoate, 4'-cyanobiphenyl 4-(2-acryloyloxyethyloxy) benzoate, 4'-cyanobiphenyl 4-(2-methacryloyloxyethyloxy) benzoate, 3',4'-difluorophenyl 4-(2-methacryloyloxyethyloxy)benzoate, naphthyl 4-(2-methacryloyloxyethyloxy)benzoate, 4-acryloyloxy-4'-decylbiphenyl, 4-acryloyloxy-4'-cyanobiphenyl, 4-(2-acryloyloxyethyloxy)-4'-cyanobiphenyl, 4-(2-methacryloyloxyethyloxy)-4'-methoxybiphenyl, 4-(2-methacryloyloxyethyloxy)-4'-(4"-fluorobenzyloxy)-biphenyl, 4-acryloyloxy-4'-propylcyclohexylphenyl, 4-methacryloyl-4'-butylbicyclohexyl, 4-acryloyl-4'-amyltolane, 4-acryloyl-4'-(3,4-difluorophenyl)bicyclohexyl, (4-amylphenyl) 4-(2-acryloyloxyethyl)benzoate, (4-(4'-propylcyclohexyl)phenyl) 4-(2-acryloyloxyethyl)benzoate, and the like.

A polyfunctional monomer that includes a plurality of polymerizable unsaturated groups (e.g., acryloyl group, methacryloyl group, vinyl group, and allyl group) may also be used as the additional copolymerizable monomer.

Examples of such a polyfunctional monomer include an alkanediol diacrylate such as 1,2-butanediol diacrylate, 1,3-butanediol diacrylate, 1,4-butanediol diacrylate, neopentanediol diacrylate, and 1,6-hexanediol diacrylate; an alkanediol dimethacrylate such as 1,2-butanediol dimethacrylate, 1,3-butanediol dimethacrylate, 1,4-butanediol dimethacrylate, neopentanediol dimethacrylate, and 1,6-hexanediol dimethacrylate; a polyethylene glycol diacrylate such as ethylene glycol diacrylate, diethylene glycol diacrylate, triethylene glycol diacrylate, and tetraethylene glycol diacrylate; a polypropylene glycol diacrylate such as propylene glycol diacrylate, dipropylene glycol diacrylate, tripropylene glycol diacrylate, and tetrapropylene glycol diacrylate; a polyethylene glycol dimethacrylate such as ethylene glycol dimethacrylate, diethylene glycol dimethacrylate, triethylene glycol dimethacrylate, and tetraethylene glycol dimethacrylate; a polypropylene glycol dimethacrylate such as propylene glycol dimethacrylate, dipropylene glycol dimethacrylate, tripropylene glycol dimethacrylate, and tetrapropylene glycol dimethacrylate; a polyethylene glycol divinyl ether such as ethylene glycol divinyl ether, diethylene glycol divinyl ether, triethylene glycol divinyl ether, and tetraethylene glycol divinyl ether; a polyethylene glycol diallyl ether such as ethylene glycol diallyl ether, diethylene glycol diallyl ether, triethylene glycol diallyl ether, and tetraethylene glycol diallyl ether; bisphenol F ethoxylate diacrylate; bisphenol F ethoxylate dimethacrylate; bisphenol A ethoxylate diacrylate; bisphenol A ethoxylate dimethacrylate; trimethylolpropane triacrylate; trimethylolpropane trimethacrylate; trimethylolpropane ethoxylate triacrylate; trimethylolpropane ethoxylate trimethacrylate; trimethylolpropane propoxylate triacrylate; trimethylolpropane propoxylate trimethacrylate; isocyanuric acid ethoxylate triacrylate; glycerol ethoxylate triacrylate; glycerol propoxylate triacrylate; pentaerythritol ethoxylate tetraacrylate; ditrimethylolpropane ethoxylate tetraacrylate; dipentaerythritol ethoxylate hexaacrylate; and the like.

The polymerizable compound according to one embodiment of the invention may be (co)polymerized optionally together with the additional copolymerizable monomer in the presence of an appropriate initiator. The initiator may be used in a ratio identical to that of the initiator included in the polymerizable composition.

When the polymer according to one embodiment of the invention is a copolymer of the polymerizable compound according to one embodiment of the invention and the additional copolymerizable monomer, the content of structural units derived from the polymerizable compound according to one embodiment of the invention is not particularly limited, but is preferably 0.1 to 50 wt %, and more preferably 1 to 40 wt %, based on the total structural units. When the content of structural units derived from the polymerizable compound is within the above range, a polymer that has a high glass transition temperature (Tg) and high hardness can be obtained.

The polymer (1) may be produced by (A) (co)polymerizing the polymerizable compound optionally together with the additional copolymerizable monomer in an appropriate organic solvent in the presence of an appropriate initiator, isolating the target polymer, dissolving the polymer in an appropriate organic solvent to prepare a solution, applying the solution to an appropriate substrate to obtain a film, and drying the film, followed by optional heating, or (B) applying a solution prepared by dissolving the polymerizable compound and an initiator in an organic solvent optionally together with the additional copolymerizable monomer to a substrate using a known coating method, removing the solvent, and effecting polymerization by applying heat or activated energy rays, for example.

Examples of the initiator include those mentioned above in connection with the initiator included in the polymerizable composition.

The organic solvent used for polymerization when implementing the method (A) is not particularly limited as long as the organic solvent is inert. Examples of the organic solvent include an aromatic hydrocarbon such as toluene, xylene, and mesitylene; a ketone such as cyclohexanone, cyclopentanone, and methyl ethyl ketone; an acetate such as butyl acetate and amyl acetate; a halogenated hydrocarbon such as chloroform, dichloromethane, and dichloroethane; an ether such as cyclopentyl methyl ether, tetrahydrofuran, and tetrahydropyran; and the like. It is preferable to use a compound having a boiling point of 60 to 250° C., and more preferably 60 to 150° C., from the viewpoint of handling capability.

Examples of the organic solvent used to dissolve the polymer when implementing the method (A), and the organic solvent used when implementing the method (B), include a ketone-based solvent such as acetone, methyl ethyl ketone, methyl isobutyl ketone, cyclopentanone, and cyclohexanone; an ester-based solvent such as butyl acetate and amyl acetate; a halogenated hydrocarbon-based solvent such as dichloromethane, chloroform, and dichloroethane; an ether-based solvent such as tetrahydrofuran, tetrahydropyran, 1,2-dimethoxyethane, 1,4-dioxane, cyclopentyl methyl ether, and 1,3-dioxolane; an aprotic polar solvent such as N,N-dimethylformamide, N,N-dimethylacetamide, dimethyl sulfoxide, gamma-butyrolactone, and N-methylpyrrolidone; and the like. Among these, a compound having a boiling point of 60 to 200° C. is preferable from the viewpoint of handling capability. These solvents may be used either alone or in combination.

A substrate formed of a known organic or inorganic material may be used as the substrate. Examples of the organic material include a polycycloolefin (e.g., Zeonex and Zeonor (registered trademark; manufactured by Zeon Corporation); Arton (registered trademark; manufactured by JSR Corporation); and Apel (registered trademark; manufactured by Mitsui Chemicals Inc.)), polyethylene terephthalate, a polycarbonate, a polyimide, a polyamide, polymethyl methacrylate, polystyrene, polyvinyl chloride, polytetrafluoroethylene, cellulose, cellulose triacetate, polyethersulfone, and the like. Examples of the inorganic material include silicon, glass, calcite, and the like. It is preferable to use a substrate formed of an organic material.

The substrate may be a single-layer substrate, or may be a laminate.

The substrate is preferably a substrate formed of an organic material, and more preferably a resin film that is formed of the organic material.

The polymer solution (method (A)) or the solution subjected to polymerization (method (B)) may be applied to the substrate using a known coating method. Examples of the coating method include a curtain coating method, an extrusion coating method, a roll coating method, a spin coating method, a dip coating method, a bar coating method, a spray coating method, a slide coating method, a print coating method, and the like.

(2) Polymer Obtained by Polymerizing Polymerizable Composition

The polymer according to one embodiment of the invention can be easily obtained by polymerizing the polymerizable composition according to one embodiment of the invention. It is preferable to use the polymerizable composition that includes the initiator (particularly a photoinitiator) in order to more efficiently effect polymerization.

Specifically, it is preferable to produce the polymer according to one embodiment of the invention using the method (B) that applies the polymerizable composition according to one embodiment of the invention to a substrate, and polymerizes the applied polymerizable composition. Examples of the substrate include a substrate that is used to produce an optically anisotropic product (described later), and the like.

The polymerizable composition according to one embodiment of the invention may be applied to the substrate using a known coating method (e.g., bar coating method, spin coating method, roll coating method, gravure coating method, spray coating method, die coating method, cap coating method, or dipping method). A known organic solvent may be added to the polymerizable composition according to one embodiment of the invention in order to improve the applicability of the polymerizable composition. In this case, it is preferable to remove the organic solvent by natural drying, drying by heating, drying under reduced pressure, drying by heating under reduced pressure, or the like, after applying the polymerizable composition to the substrate.

The polymerizable compound according to one embodiment of the invention or the polymerizable composition according to one embodiment of the invention may be polymerized by applying activated energy rays, or utilizing a thermal polymerization method, for example. It is preferable to polymerize the polymerizable compound or the polymerizable composition by applying activated energy rays since heating is unnecessary (i.e., the reaction can be effected at room temperature). It is preferable to apply light (e.g., ultraviolet rays) to the polymerizable compound or the polymerizable composition since the operation is simple.

The temperature during the application of light is preferably set to 30° C. or less. The irradiance is normally set to 1 W/m$^2$ to 10 kW/m$^2$, and preferably 5 W/m$^2$ to 2 kW/m$^2$.

A polymer obtained by polymerizing the polymerizable compound according to one embodiment of the invention or the polymerizable composition according to one embodiment of the invention may be removed from the substrate, and used alone, or may be used directly as an optical film organic material or the like without removing it from the substrate.

The number average molecular weight of the polymer according to one embodiment of the invention thus obtained is preferably 500 to 500,000, and more preferably 5,000 to 300,000. When the number average molecular weight of the polymer is within the above range, the resulting film exhibits high hardness and an excellent handling capability. The number average molecular weight of the polymer may be determined by gel permeation chromatography (GPC) using monodisperse polystyrene as the standard (eluent: tetrahydrofuran).

It is considered that the polymer according to one embodiment of the invention has a structure in which cross-linking points are uniformly present within the molecule, and exhibits a high cross-linking efficiency and excellent hardness.

The polymer according to one embodiment of the invention makes it possible to inexpensively produce an optical film that achieves uniform conversion of polarized light over a wide wavelength band, and exhibits satisfactory performance.

4) Optically Anisotropic Product

An optically anisotropic product according to one embodiment of the invention includes (is produced using) the polymer according to one embodiment of the invention.

The optically anisotropic product according to one embodiment of the invention may be obtained by forming an alignment film on a substrate, and forming a polymer film on the alignment film using the polymer according to one embodiment of the invention.

The alignment film is formed on the surface of the substrate in order to achieve the in-plane alignment of an organic semiconductor compound in one direction.

The alignment film may be obtained by applying a solution (alignment film composition) that includes a polymer (e.g., polyimide, polyvinyl alcohol, polyester, polyallylate, polyamideimide, or polyetherimide) to the substrate to form a film, drying the film, and subjecting the film to a rubbing treatment in one direction, for example.

The thickness of the alignment film is preferably 0.001 to 5 μm, and more preferably 0.001 to 1 μm.

The rubbing treatment may be performed on the alignment film or the substrate. The rubbing treatment may be implemented using an arbitrary method. For example, the alignment film may be rubbed in a given direction using a roll around which a cloth or felt formed of synthetic fibers (e.g., nylon) or natural fibers (e.g., cotton) is wound. It is preferable to wash (clean) the alignment film with isopropyl alcohol or the like after completion of the rubbing treatment in order to remove a fine powder (foreign substance) formed during the rubbing treatment, and clean the surface of the alignment film.

It is also possible to provide the alignment film with a function of achieving in-plane alignment in one direction by applying polarized ultraviolet rays to the surface of the alignment film.

The liquid crystal layer may be formed on the alignment film using the polymer according to one embodiment of the invention by utilizing the method described above in connection with the polymer according to one embodiment of the invention.

Since the optically anisotropic product according to one embodiment of the invention is produced using the polymer according to one embodiment of the invention, the optically anisotropic product can be produced at low cost, achieves uniform conversion of polarized light over a wide wavelength band, and exhibits satisfactory performance.

Examples of the optically anisotropic product according to one embodiment of the invention include a retardation film, an alignment film for a liquid crystal display device (liquid crystal display), a polarizer, a viewing angle enhancement film, a color filter, a low-pass filter, an optical polarization prism, an optical filter, and the like.

EXAMPLES

The invention is further described below by way of examples. Note that the invention is not limited to the following examples.

Example 1: Synthesis of Compound 1

Compound 1

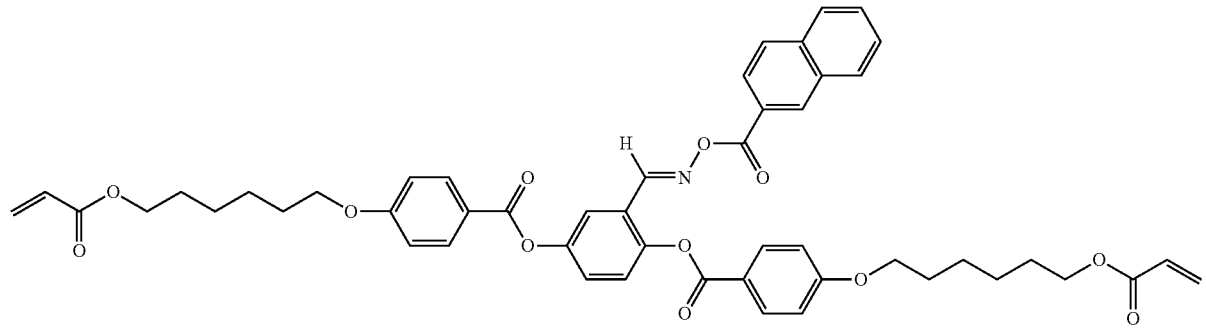

Step 1: Synthesis of Intermediate A

Intermediate A

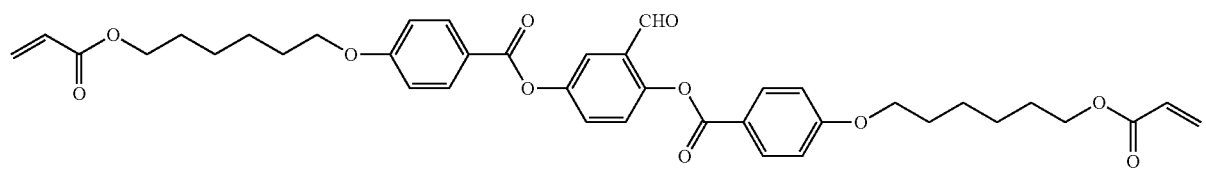

A four-necked reactor equipped with a thermometer was charged with 20 g (144.8 mmol) of 2,5-dihydroxybenzaldehyde, 105.8 g (362.0 mmol) of 4-(6-acryloylhex-1-yloxy) benzoic acid (manufactured by DKSH Japan K.K.), 5.3 g (43.4 mmol) of 4-(dimethylamino)pyridine, and 200 ml of N-methylpyrrolidone under a nitrogen stream to prepare a solution. After the addition of 83.3 g (434.4 mmol) of 1-ethyl-3-(3-dimethylaminopropyl)carbodiimide hydrochloride (WSC) to the solution, the mixture was stirred at 25° C. for 12 hours. After completion of the reaction, the reaction mixture was added to 1.5l of water, followed by extraction with 500 ml of ethyl acetate. The ethyl acetate layer was dried over anhydrous sodium sulfate, and sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=9:1 (volume ratio (hereinafter the same))) to obtain 75 g of an intermediate A as a white solid (yield: 75.4%).

The structure of the target product was identified by $^1$H-NMR.

$^1$H-NMR (400 MHz, CDCl$_3$, TMS, δ ppm): 10.20 (s, 1H), 8.18-8.12 (m, 4H), 7.78 (d, 1H, J=2.8 Hz), 7.52 (dd, 1H, J=2.8 Hz, 8.7 Hz), 7.38 (d, 1H, J=8.7 Hz), 7.00-6.96 (m, 4H), 6.40 (dd, 2H, J=1.4 Hz, 17.4 Hz), 6.12 (dd, 2H, J=10.6 Hz, 17.4 Hz), 5.82 (dd, 2H, J=1.4 Hz, 10.6 Hz), 4.18 (t, 4H, J=6.4 Hz), 4.08-4.04 (m, 4H), 1.88-1.81 (m, 4H), 1.76-1.69 (m, 4H), 1.58-1.42 (m, 8H)

Step 2: Synthesis of Intermediate B

A four-necked reactor equipped with a thermometer was charged with 4.00 g (5.82 mmol) of the intermediate A synthesized in the step 1 and 50 ml of acetonitrile under a nitrogen stream to prepare a solution. After the addition of 608 mg (8.74 mmol) of hydroxylamine chloride to the solution, the mixture was stirred at 50° C. for 9 hours. The reaction mixture was added to 300 ml of water, followed by extraction three times with 100 ml of ethyl acetate. The ethyl acetate layer was collected, washed with 100 ml of a saturated sodium chloride solution, and dried over anhydrous sodium sulfate, and sodium sulfate was filtered off. Ethyl acetate was evaporated from the filtrate under reduced pressure using a rotary evaporator to obtain a white solid. The white solid was purified by silica gel column chromatography (toluene:ethyl acetate=9:1) to obtain 2.24 g of an intermediate B as a white solid (yield: 54.8%).

The structure of the target product was identified by $^1$H-NMR.

$^1$H-NMR (400 MHz, CDCl$_3$, TMS, δ ppm): 8.23 (s, 1H), 8.14 (d, 2H, J=8.8 Hz), 8.13 (d, 2H, J=8.8 Hz), 7.70 (d, 1H, J=2.4 Hz), 7.48 (s, 1H), 7.29 (dd, 1H, J=2.4 Hz, 8.8 Hz), 7.23 (d, 1H, J=8.8 Hz), 6.98 (d, 2H, J=8.8 Hz), 6.96 (d, 2H, J=8.8 Hz), 6.40 (dd, 2H, J=1.6 Hz, 17.2 Hz), 6.12 (dd, 2H, J=10.8 Hz, 17.2 Hz), 5.82 (dd, 2H, J=1.6 Hz, 10.8 Hz), 4.18 (t, 4H, J=6.4 Hz), 4.06 (t, 2H, J=6.4 Hz), 6.05 (t, 2H, J=6.4 Hz), 1.80-1.88 (m, 4H), 1.69-1.76 (m, 4H), 1.43-1.55 (m, 8H)

Step 3: Synthesis of Compound 1

A four-necked reactor equipped with a thermometer was charged with 1.12 g (1.60 mmol) of the intermediate B synthesized in the step 2 and 20 ml of tetrahydrofuran under a nitrogen stream to prepare a solution. After cooling the solution to 0° C., 458 mg (2.40 mmol) of 2-naphthoyl chloride and 290 mg (2.88 mmol) of triethylamine were added to the solution. The mixture was then stirred at 25° C. for 3 hours. After completion of the reaction, the reaction mixture was added to 300 ml of water, followed by extraction three times with 100 ml of ethyl acetate. The ethyl acetate layer was collected, washed with 200 ml of a saturated sodium chloride solution, and dried over anhydrous sodium sulfate, and sodium sulfate was filtered off. Ethyl acetate was evaporated from the filtrate under reduced pressure using a rotary evaporator to obtain a light yellow solid. The light yellow solid was purified by silica gel column chromatography (n-hexane:ethyl acetate=7:3) to obtain 1.11 g of a compound 1 as a white solid (yield: 81.1%).

Intermediate B

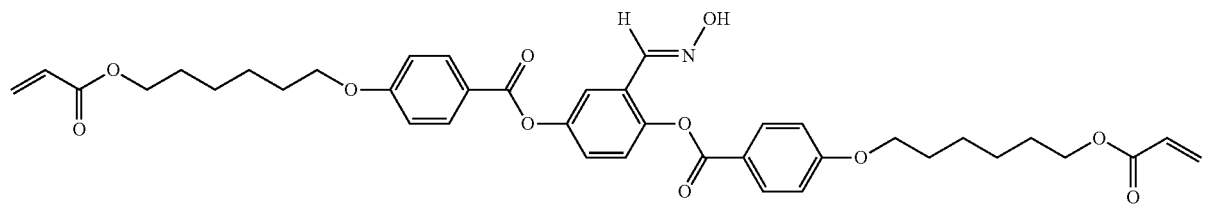

The structure of the target product was identified by $^1$H-NMR.

$^1$H-NMR (400 MHz, CDCl$_3$, TMS, δ ppm): 8.73 (s, 1H), 8.66 (s, 1H), 8.21 (d, 2H, J=8.8 Hz), 8.14 (d, 2H, J=8.8 Hz), 8.06-8.09 (m, 2H), 7.95 (d, 1H, J=7.6 Hz), 7.89 (d, 1H, J=8.8 Hz), 7.87 (d, 1H, J=7.6 Hz), 7.60 (ddd, 1H, J=1.6 Hz, 8.4 Hz, 8.8 Hz), 7.54 (ddd, 1H, J=1.6 Hz, 7.6 Hz, 8.4 Hz), 7.45 (dd, 1H, J=2.4 Hz, 8.8 Hz), 7.34 (d, 1H, J=8.8 Hz), 7.02 (d, 2H, J=8.8 Hz), 6.98 (d, 2H, J=8.8 Hz), 6.401 (dd, 1H, J=1.6 Hz, 17.2 Hz), 6.396 (dd, 1H, J=1.6 Hz, 17.2 Hz), 6.123 (dd, 1H, J=10.4 Hz, 17.2 Hz), 6.115 (dd, 1H, J=10.4 Hz, 17.2 Hz), 5.82 (dd, 1H, J=1.6 Hz, 10.4 Hz), 5.81 (dd, 1H, J=1.6 Hz, 10.4 Hz), 4.182 (t, 2H, J=6.8 Hz), 4.176 (t, 2H, J=6.4 Hz), 4.07 (t, 2H, J=6.4 Hz), 4.06 (t, 2H, J=6.4 Hz), 1.81-1.88 (m, 4H), 1.68-1.76 (m, 4H), 1.44-1.58 (m, 8H)

The phase transition temperature was measured as described below using the compound 1 obtained in Example 1 and a compound 1r ("LC242" manufactured by BASF) (see below).

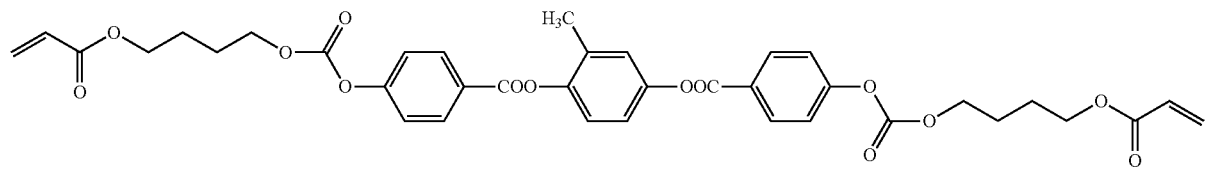

Compound 1r

Measurement of Phase Transition Temperature 10 mg of each compound (compounds 1 and 1r) was weighed, and placed in a solid state between two glass substrates provided with a polyimide alignment film subjected to a rubbing treatment (manufactured by E.H.C. Co. Ltd.). The substrates were placed on a hot plate, heated from 40° C. to 200° C., and cooled to 40° C. A change in structure when the temperature was changed was observed using a polarizing microscope ("ECLIPSE LV100 POL" manufactured by Nikon Corporation).

The phase transition temperature measurement results are shown in Table 1. In Table 1, "C" refers to "crystal", "N" refers to "nematic", and "I" refers to "isotropic". The term "crystal" means that the test compound was in a solid phase, the term "nematic" means that the test compound was in a nematic liquid crystal phase, and the term "isotropic" means that the test compound was in an isotropic liquid phase. The example in which the compound 1r was used is referred to as "Reference Example 1".

TABLE 1

| | Compound | Phase transition temperature |
|---|---|---|
| Example 1 | Compound 1 | C ⇌ (40° C. or less) N ⇌ (94° C. / 74° C.) I |
| Reference Example 1 | Compound 1r | C ⇌ (40° C. or less) N ⇌ (123° C. / 122° C.) I (60° C.) |

Example 2

1.0 g of the compound 1 obtained in Example 1, 30 mg of Adekaoptomer N-1919 (manufactured by Adeka Corporation) (photoinitiator), and 100 mg of a 1% cyclopentanone solution of KH-40 (manufactured by AGC Seimi Chemical Co., Ltd.) (surfactant) were dissolved in 2.3 g of cyclopentanone. The resulting solution was filtered through a disposable filter having a pore size of 0.45 μm to prepare a polymerizable composition 1.

Reference Example 2

A polymerizable composition 2 was prepared substantially in the same manner as in Example 2, except that the compound 1r was used instead of the compound 1.

Measurement of Retardation and Evaluation of Wavelength Dispersion

Formation of Liquid Crystal Layer Using Polymerizable Composition

Each polymerizable composition (polymerizable composition 1 obtained in Example 2 and polymerizable composition 2 obtained in Reference Example 2) was applied to a transparent glass substrate provided with a polyimide alignment film subjected to a rubbing treatment (manufactured by E.H.C. Co., Ltd.) using a #4 wire bar. The resulting film was dried for 1 minute at the temperature shown in Table 2, and subjected to an alignment treatment for 1 minute at the temperature shown in Table 2 to form a liquid crystal layer. Ultraviolet rays were applied to the liquid crystal layer in air at a dose of 1,500 mJ/cm$^2$ to effect polymerization to prepare a wavelength dispersion measurement sample.

(ii) Measurement of Retardation

The retardation between 400 nm and 800 nm was measured using the sample utilizing an ellipsometer ("M2000U" manufactured by J. A. Woollam).

(iii) Evaluation of Wavelength Dispersion

The wavelength dispersion was evaluated based on the values $\alpha$ and $\beta$ that were calculated as described below using the measured retardation.

$\alpha$=(retardation at 449.9 nm)/(retardation at 548.5 nm)

$\beta$=(retardation at 650.2 nm)/(retardation at 548.5 nm)

Table 2 shows the thickness (μm) of the liquid crystal polymer film obtained by polymerizing the polymerizable composition, the retardation (Re) at a wavelength of 548.5 nm, and the values $\alpha$ and $\beta$.

TABLE 2

| | Polymerizable composition | Polymerizable compound | Drying temperature (° C.) | Alignment treatment temperature (° C.) |
|---|---|---|---|---|
| Example 2 | 1 | Compound 1 | 120 | 23 |
| Reference Example 2 | 2 | Compound 1r | 80 | 23 |

| | Thickness (μm) | Re (548.5 nm) | $\alpha$ | $\beta$ | Wavelength dispersion |
|---|---|---|---|---|---|
| Example 2 | 1.572 | 196.45 | 0.921 | 0.999 | Flat wavelength dispersion |
| Reference Example 2 | 1.481 | 223.10 | 1.087 | 0.970 | Normal wavelength dispersion |

The value $\alpha$ is smaller than 1, and the value $\beta$ is larger than 1 when ideal wideband wavelength dispersion (reverse wavelength dispersion) is achieved. The value $\alpha$ and the value β are almost identical to each other when flat wavelength dispersion is achieved. The value α is larger than 1, and the value β is smaller than 1 when normal dispersion is achieved. Flat wavelength dispersion that ensures that the values α and β are almost identical to each other is preferable, and reverse wavelength dispersion that ensures that the value a is smaller than 1, and the value β is larger than 1, is particularly preferable.

As is clear from the results shown in Table 2, the optically anisotropic product obtained using the compound 1 obtained in Example 1 had flat wavelength dispersion.

The invention claimed is:

1. A compound represented by a formula (3),

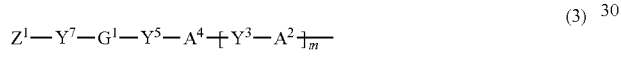
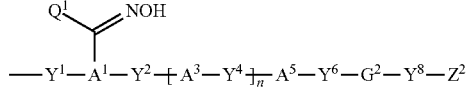

wherein each of $Y^1$ to $Y^8$ independently represents a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$—, or —NR$^1$—O—, R$^1$ represents a hydrogen atom or an alkyl group having 1 to 6 carbon atoms, each of $G^1$ and $G^2$ independently represents a substituted or unsubstituted divalent linear aliphatic group having 1 to 20 carbon atoms that optionally includes —O—, —S—, —O—C(=O)—, —C(=O)—O—, —O—C(=O)—O—, —NR$^3$—C(=O)—, —C(=O)—NR$^3$—, —NR$^3$—, or —C(=O)—, provided that a case where the linear aliphatic group includes two or more contiguous —O— or —S— is excluded, R$^3$ represents a hydrogen atom or an alkyl group having 1 to 6 carbon atoms, each of $Z^1$ and $Z^2$ independently represents an alkenyl group having 2 to 10 carbon atoms that is substituted with a halogen atom, or unsubstituted, A$^1$ represents a substituted or unsubstituted trivalent aromatic group, each of $A^2$ and $A^3$ independently represents a substituted or unsubstituted divalent alicyclic hydrocarbon group having 3 to 30 carbon atoms, each of $A^4$ and $A^5$ independently represents a substituted or unsubstituted divalent aromatic group having 6 to 30 carbon atoms, Q$^1$ represents a substituted or unsubstituted alkyl group having 1 to 6 carbon atoms, an organic group having 2 to 30 carbon atoms that includes at least one aromatic ring selected from the group consisting of an aromatic hydrocarbon ring and a heteroaromatic ring, or a hydrogen atom, and each of n and m independently represents 0 or 1.

2. A compound represented by a formula (6),

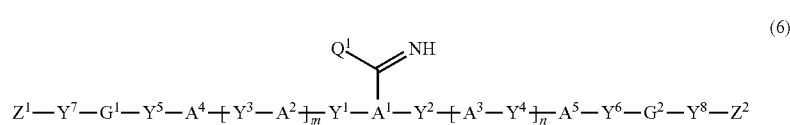

wherein each of $Y^1$ to $Y^8$ independently represents a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$—, or —NR$^1$—O—, R$^1$ represents a hydrogen atom or an alkyl group having 1 to 6 carbon atoms, each of $G^1$ and $G^2$ independently represents a substituted or unsubstituted divalent linear aliphatic group having 1 to 20 carbon atoms that optionally includes —O—, —S—, —O—C(=O)—, —C(=O)—O—, —O—C(=O)—O—, —NR$^3$—C(=O)—, —C(=O)—NR$^3$—, —NR$^3$—, or —C(=O)—, provided that a case where the linear aliphatic group includes two or more contiguous —O— or —S— is excluded, R$^3$ represents a hydrogen atom or an alkyl group having 1 to 6 carbon atoms, each of $Z^1$ and $Z^2$ independently represents an alkenyl group having 2 to 10 carbon atoms that is substituted with a halogen atom, or unsubstituted, A$^1$ represents a substituted or unsubstituted trivalent aromatic group, each of $A^2$ and $A^3$ independently represents a substituted or unsubstituted divalent alicyclic hydrocarbon group having 3 to 30 carbon atoms, each of $A^4$ and $A^5$ independently represents a substituted or unsubstituted divalent aromatic group having 6 to 30 carbon atoms, Q$^1$ represents a substituted or unsubstituted alkyl group having 1 to 6 carbon atoms, an organic group having 2 to 30 carbon atoms that includes at least one aromatic ring selected from the group consisting of an aromatic hydrocarbon ring and a heteroaromatic ring, or a hydrogen atom, and each of n and m independently represents 0 or 1.

* * * * *